(12) United States Patent
Robinson et al.

(10) Patent No.: US 6,380,219 B1
(45) Date of Patent: Apr. 30, 2002

(54) ARYLSULFONYLAMINO HYDROXAMIC ACID DERIVATIVES

(75) Inventors: Ralph P. Robinson, Gales Ferry, CT (US); James P. Rizzi, Niwot, CO (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/635,186

(22) Filed: Aug. 8, 2000

Related U.S. Application Data

(62) Division of application No. 09/406,522, filed on Sep. 28, 1999, now Pat. No. 6,147,074, which is a division of application No. 09/122,920, filed on Jul. 27, 1998, now Pat. No. 5,994,351, which is a division of application No. 08/894,873, filed on Mar. 7, 1996, now Pat. No. 5,863,949.

(51) Int. Cl.$^7$ .................. A61K 31/4468; A61P 19/02; C07D 211/66
(52) U.S. Cl. ............... 514/329; 546/223; 562/430; 562/622
(58) Field of Search ................ 562/622, 430; 546/223; 514/329

(56) References Cited

FOREIGN PATENT DOCUMENTS

| EP | 606046 | * | 7/1994 |
|---|---|---|---|
| WO | 9005719 | * | 5/1940 |

* cited by examiner

*Primary Examiner*—Robert W. Ramsuer
(74) *Attorney, Agent, or Firm*—Peter C. Richardson; Paul H. Ginsburg; Garth Butterfield

(57) ABSTRACT

A compound of the formula

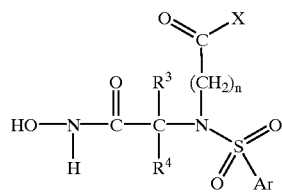

I wherein n, X, $R^3$, $R^4$ and Ar are as defined above, useful in the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of TNF.

7 Claims, No Drawings

ARYLSULFONYLAMINO HYDROXAMIC ACID DERIVATIVES

This application is a divisional of Ser. No. 09/406,522 filed Sep. 28, 1999 now U.S. Pat. No. 6,147,074 which is a divisional of Ser. No. 09/122,920 filed Jul. 27, 1998, now U.S. Pat. No. 5,994,351, which is a divisional of Ser. No. 08/894,873 Mar. 7, 1996 now U.S. Pat. No. 5,863,944.

BACKGROUND OF THE INVENTION

The present invention relates to arylsulfonylamino hydroxamic acid derivatives which are inhibitors of matrix metalloproteinases or the production of tumor necrosis factor (hereinafter also referred to as TNF) and as such are useful in the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of TNF.

This invention also relates to a method of using such compounds in the treatment of the above diseases in mammals, especially humans, and to the pharmaceutical compositions useful therefor.

There are a number of enzymes which effect the breakdown of structural proteins and which are structurally related metalloproteases. Matrix-degrading metalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, as well as HIV-infection (*J. Leuk. Biol.*, 52 (2): 244–248, 1992).

Tumor necrosis factor is recognized to be involved in many infectious and auto-immune diseases (W. Friers, *FEBS Letters*, 1991, 285, 199). Furthermore, it has been shown that TNF is the prime mediator of the inflammatory response seen in sepsis and septic shock (C.E. Spooner et al., *Clinical Immunology and Immunopathology*, 1992, 62 S11).

SUMMARY OF THE INVENTION

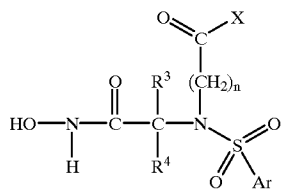

I or the pharmaceutically acceptable salts thereof, wherein n is 1 to 6;

X is hydroxy, $(C_1-C_6)$alkoxy or $NR^1R^2$ wherein $R^1$ and $R^2$ are each independently selected from the group consisting of hydrogen, $(C_1-C_6)$alkyl, piperidyl, $(C_1-C_6)$alkylpiperidyl, $(C_8-C_{10})$arylpiperidyl, $(C_5-C_9)$heteroarylpiperidyl, $(C_6-C_{10})$aryl$(C_1-C_6)$alkylpiperidyl, $(C_5-C_9)$heteroaryl,$(C_6-C_{10})$aryl$(C_1-C_6)$alykyl,$(C_5-C_9)$heteroaryl$(C_1-C_6)$alkyl,$(C_6-C_{10})$aryl$(C_6-C_{10})$aryl, $(C_5-C_{10})$aryl$(C_6-C_{10})$aryl$(C_1-C_5)$alkyl, $(C_3-C_6)$cycloalkyl, $(C_3-C_6)$cycloalkyl$(C_1-C_6)$alkyl, $R^5(C_2-C_5)$alkyl, $(C_1-C_5)$alkyl$(CHR^5)(C_1-C_5)$alkyl wherein $R^5$ is hydroxy, $(C_1-C_6)$acyloxy, $(C_1-C_6)$alkoxy, piperazino, $(C_1-C_6)$acylamino, $(C_5-C_{10})$aryithio, $(C_1-C_5)$alkylsulfinyl, $(C_5-C_{10})$arylsulfinyl, $(C_1-C_8)$alkylsulfoxyl, $(C_6-C_{10})$arylsulfoxyl, amino, $(C_1-C_5)$alkylamino,$((C_1-C_5)$alkyl$)_2$amino,$(C_1-C_5)$acylpiperazino, $(C_1-C_6)$aklylpiperazino, $(C_6-C_{10})$aryl$(C_1-C_5)$alkylpiperazino, $(C_5-C_9)$heteroaryl$(C_1-C_6)$alkylpiperazino, morpholino, thiomorpholino, piperidino or pyrrolidino;$R^5(C_1-C_6)$alkyl,$(C_1-C_5)$alkyl$(CHR^5)(C_1-C_6)$alkyl wherein $R^5$ is piperidyl, $(C_1-C_6)$alkylpiperidyl, $(C_6-C_{10})$arylpiperidyl, $(C_6-C_{10})$aryl$(C_1-C_6)$alkylpiperidyl, $(C_5-C_9)$heteroarylpiperidyl or $(C_5-C_9)$heteroaryl$(C_1-C_6)$alkylpiperidyl; and $CH(R^7)COR^8$ wherein $R^7$ is hydrogen, $(C_1-C_5)$alkyl, $(C_5-C_{10})$aryl$(C_1-C_5)$alkyl, $(C_5-C_9)$heteroaryl$(C_1-C_6)$alkyl, $(C_1-C_6)$alkylthio $(C_1-C_5)$alkyl, $(C_5-C_{10})$arylthio$(C_1-C_5)$alkyl, $(C_1-C_6)$alkylsulfinyl $(C_1-C_6)$alkyl, $(C_5-C_{10})$arylsulfinyl$(C_1-C_6)$alkyl, $(C_1-C_5)$alkylsulfonyl$(C_1-C_6)$alkyl, $(C_6-C_{10})$arylsulfonyl $(C_1-C_6)$alkyl, hydroxy$(C_1-C_6)$alkyl, amino$(C_1-C_6)$alkyl, $(C_1-C_6)$alkylamino$(C_1-C_6)$alkyl, $((C_1-C_5)$alkylamino$)_2(C_1-C_6)$alkyl,$R^9R^{10}NCO(C_1-C_6)$alkyl or $R^9OCO(C_1-C_5)$alkyl wherein $R^9$ and $R^{10}$ are each independently selected from the group consisting of hydrogen, $(C_1-C_5)$alkyl, $(C_5-C_{10})$aryl$(C_1-C_5)$alkyl and $(C_5-C_9)$heteroaryl$(C_1-C_6)$alkyl; and $R^8$ is $R^{11}O$ or $R^{11}R^{12}N$ wherein $R^{11}$ and $R^{12}$ are each independently selected from the group consisting of hydrogen, $(C_1-C_5)$alkyl, $(C_5-C_{10})$aryl$(C_1-C_6$alkyl and $(C_5-C_9)$heteroaryl$(C_1-C_6)$alkyl;

or $R^1$ and $R^2$, or $R^9$ and $R^{10}$, or $R^{11}$ and $R^{12}$ may be taken together to form an azetidinyl, pyrrolidinyl, morpholinyl, thiomorpholinyl, indolinyl, isoindolinyl, tetrahydroquinolinyl, tetrahydroisoquinolinyl, $(C_1-C_6)$acylpiperazinyl, $(C_1-C_5$alkylpiperazinyl, $(C_5-C_{10})$arylpiperazinyl, $(C_5-C_9)$heterorarylpiperazinyl or a bridged diazabicycloalkyl ring selected from the group consisting of

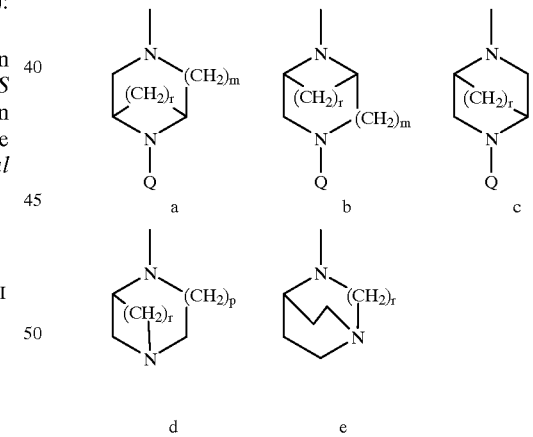

wherein r is 1, 2 or 3;

m is 1 or 2;

p is 0 or 1; and

Q is hydrogen, $(C_1-C_3)$alkyl or $(C_1-C_6)$acyl;

$R^3$ and $R^4$ are each independently selected from the group consisting of hydrogen, $(C_1-C_6)$alkyl, trifluoromethyl, trifluoromethyl$(C_1-C_6)$alkyl, $C_1-C_6)$alkyl (difluoromethylene), $(C_1-C_3)$alkyl(difluoromethylene) $(C_1-C_3)$alkyl, $(C_6-C_{10})$aryl, $(C_5-C_9)$heteroaryl, $(C_6-C_{10})$aryl$(C_1-C_5)$alkyl, $(C_5-C_9)$heteroaryl$(C_1-C_6)$alkyl, $(C_6-C_{10})$aryl $(C_5-C_{10})$aryl, $(C_6-C_{10})$aryl$(C_5-C_{10})$aryl $(C_1-C_6)$alkyl, $(C_3-C_6)$cycloalkyl, $(C_3-C_6)$cycloalkyl ($C_1$–$C_5$)alkyl, hydroxy($C_1$–$C_6$)alkyl, ($C_1$–$C_6$)acyloxy ($C_1$–$C_5$)alkyl, ($C_1$–$C_5$)alkoxy($C_1$–$C_5$)alkyl, piperazinyl ($C_1$–$C_6$)alkyl,($C_1$–$C_6$)acylamino($C_1$–$C_5$)alkyl,piperidyl, ($C_1$–$C_6$)alkylpiperidyl, ($C_5$–$C_{10}$)aryl($C_1$–$C_6$)alkoxy($C_1$–$C_6$) alkyl, ($C_5$–$C_9$)heteroaryl($C_1$–$C_6$)alkoxy($C_1$–$C_6$)alkyl, ($C_1$–$C_6$)alkylthio($C_1$–$C_5$)alkyl,($C_5$–$C_{10}$)arylthio($C_1$–$C_6$) alkyl,($C_1$–$C_6$)alkylsulfinyl($C_1$–$C_6$)alkyl, ($C_6$–$C_{10}$) arylsulfinyl($C_1$–$C_5$)alkyl, ($C_1$–$C_6$)alkylsulfonyl($C_1$–$C_6$) alkyl, ($C_6$–$C_{10}$)arylsulfonyl ($C_1$–$C_6$)alkyl, amino($C_1$–$C_6$) alkyl, ($C_1$–$C_6$)alkylamino($C_1$–$C_6$)alkyl, (($C_1$–$C_5$) alkylamino)$_2$($C_1$–$C_5$)alkyl, $R^{13}CO(C_1$–$C_5$)alkyl wherein $R^{13}$ is $R^{20}O$ or $R^{20}R^{21}N$ wherein $R^{20}$ and $R^{21}$ are each independently selected from the group consisting of hydrogen, ($C_1$–$C_5$)alkyl, ($C_6$–$C_{10}$)aryl($C_1$–$C_6$)alkyl or ($C_5$–$C_9$)heteroaryl($C_1$–$C_5$)alkyl; or $R^{14}(C_1$–$C_5$)alkyl wherein $R^{14}$ is ($C_1$–$C_6$)acylpiperazino, ($C_5$–$C_{10}$) arylpiperazino, ($C_5$–$C_9$)heteroarylpiperazino, ($C_1$–$C_6$) alkylpiperazino, morpholino, thiomorpholino, piperidino, pyrrolidino, piperidyl, ($C_1$–$C_6$)alkylpiperidyl, ($C_5$–$C_9$) heteroaryl($C_1$–$C_6$)alkylpiperidyl or ($C_1$–$C_6$)acylpiperidyl;

or $R^3$ and $R^4$, or $R^{20}$ and $R^{21}$ may be taken together to form a ($C_3$–$C_6$)cycloalkyl, oxacyclohexyl, thiocyclohexyl, indanyl or tetralinyl ring or a group of the formula

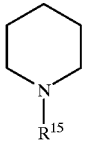

wherein $R^{15}$ is hydrogen, ($C_1$–$C_6$)acyl, ($C_1$–$C_6$alkyl, ($C_6$–$C_{10}$)aryl($C_1$–$C_6$)alkyl, ($C_5$–$C_9$)heteroary($C_1$–$C_6$)alkyl or ($C_1$–$C_6$)alkylsulfonyl; and Ar is ($C_6$–$C_{10}$)aryl, ($C_5$–$C_9$)heteroaryl, ($C_1$–$C_6$)alkyl ($C_6$–$C_{10}$)aryl, ($C_1$–$C_5$)alkoxy ($C_6$–$C_{10}$)aryl, (($C_1$–$C_6$) alkoxy)$_2$($C_6$–$C_{10}$)aryl, ($C_5$–$C_{10}$)aryloxy($C_6$–$C_{10}$)aryl, ($C_5$–$C_9$)heteroaryloxy($C_6$–$C_{10}$aaryl, ($C_1$–$C_6$)alkyl($C_5$–$C_9$) heteroaryl, ($C_1$–$C_6$)alkoxy ($C_5$–$C_9$)heteroaryl, (($C_1$–$C_5$) alkoxy)$_2$($C_5$–$C_9$)heteroaryl, ($C_6$–$C_{10}$)aryloxy($C_5$–$C_9$) heteroaryl, ($C_5$–$C_9$)heteroaryloxy($C_5$–$C_9$)heteroaryl;

with the proviso that when either $R^1$ or $R^2$ is CH($R^7$) $COR^8$ wherein $R^7$ and $R^8$ are as defined above, the other of $R^1$ or $R^2$ is hydrogen, ($C_1$–$C_6$)alkyl or benzyl.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless other wise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, ($C_1$–$C_6$)alkocxy, ($C_6$–$C_{10}$)aryloxy, trifluoromethoxy, difluoromethoxy and ($C_1$–$C_6$)alkyl.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents selected from the group consisting of fluoro, chloro, trifluoromethyl, ($C_1$–$C_6$)alkoxy, ($C_6$–$C_{10}$)aryloxy, trifluoromethoxy, difluoromethoxy and ($C_1$–$C_6$)alkyl.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

The term "acyloxy", as used herein, includes O-acyl groups wherein "acyl" is defined above.

The compound of formula I may have chiral centers and therefore exist in different enantiomeric forms. This invention relates to all optical isomers and steroisomers of the compounds of formula I and mixtures thereof.

Preferred compounds of formula I include those wherein n is 2.

Other preferred compounds of formula I include those wherein Ar is 4-methoxyphenyl or 4-phenoxyphenyl.

Other preferred compounds of formula I include those wherein either $R^3$ or $R^4$ is not hydrogen.

Other preferred compounds of formula I include those wherein n is 1 and either $R^1$ or $R^2$ is hydrogen.

Other preferred compounds of formula I includes those wherein X is hydroxy, Ar is 4-methoxyphenyl or 4-phenoxyphenyl and either $R^3$ or $R^4$ is not hydrogen.

Other preferred compounds of formula I include those wherein X is alkoky, Ar is 4-methoxyphenyl or 4-phenoxyphenyl and either $R^3$ or $R^4$ is not hydrogen.

Other preferred compounds of formula I include those wherein Ar is 4-methoxyphenyl or 4-phenoxyphenyl and $R^3$ and $R^4$ are taken together to form ($C_3$–$C_6$)cycloalkanyl, oxacyclohexanyl, thiocyclohexanyl, indanyl or a group of the formula

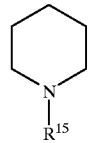

wherein $R^{15}$ is ($C_1$–$C_6$)acyl, ($C_1$–$C_6$)alkyl, ($C_5$–$C_{10}$)aryl ($C_1$–$C_6$)alkyl, ($C_5$–$C_9$)heteroaryl($C_1$–$C_6$)alkyl or ($C_1$–$C_6$) alkylsulfonyl.

More preferred compounds of formula I are those wherein n is 2, Ar is 4-methoxyphenyl or 4phenoxyphenyl, $R^1$ and $R^2$ are taken together to form piperazinyl, ($C_1$–$C_6$) alkylpiperazinyl, ($C_6$–$C_{10}$)aryl piperazinyl or ($C_5$–$C_9$) heteroaryl($C_1$–$C_6$)alkylpiperazinyl, and either $R^3$ or $R^4$ is not hydrogen or both $R^3$ and $R^4$ are not hydrogen.

More preferred compounds of formula I are those wherein n is 2, Ar is 4-methoxyphenyl or 4-phenoxyphenyl, $R^1$ is hydrogen or ($C_1$–$C_6$)alkyl, $R^2$ is 2-pyridylmethyl, 3-pyridylmethyl or 4-pyridylmethyl, and either $R^3$ or $R^4$ is not hydrogen or both $R^3$ and $R^4$ are not hydrogen.

More preferred compounds of formula I are those wherein n is 1, Ar is 4-methoxyphenyl or 4phenoxyphenyl, $R^1$ is hydrogen, $R^2$ is 2-pyridylmethyl, 3-pyridylmethyl or 4-pyridylmethyl, and either $R^3$ or $R^4$ is not hydrogen or both $R^3$ and $R^4$ are not hydrogen.

More preferred compounds of formula I are those wherein n is 2, Ar is 4-methyoxyphenyl, $R^1$ is hydrogen or ($C_1$–$C_6$) alkyl and $R^2$ is $R^5$ ($C_2$–$C_6$)alkyl wherein $R^5$ is morpholino, thiomorpholino, piperidino, pyrrolidino, ($C_1$–$C_6$) acylpiperazino, ($C_1$–$C_6$)akylpiperazino, ($C_6$–$C_{10}$) arylpiperazino, ($C_5$–$C_9$)heteroarylpiperazino, ($C_6$–$C_{10}$aryl ($C_1$–$C_6$)alkylpiperazino or ($C_5$–$C_9$)heteroaryl($C_1$–$C_6$) alkylpiperazino and either $R^3$ or $R^4$ is not hydrogen or both $R^3$ and $R^4$ are not hydrogen.

More preferred compounds of formula I are those wherein n is 1, Ar is 4-methoxyphenyl or 4-phenoxyphenyl, $R^1$ is hydrogen, $R^2$ is $R^5$ ($C_2$–$C_6$)alkyl wherein $R^5$ is morpholino, thiomorpholino, piperidino, pyrrolidino, ($C_1$–$C_6$) acylpiperazino, ($C_1$–$C_6$)akylpiperazino, ($C^5$–$C_{10}$) arylpiperazino, ($C_5$–$C_9$)heteroarylpiperazino, ($C_6$–$C_{10}$)aryl ($C_1$–$C_6$)alkylpiperazino or ($C_5$–$C_9$)heteroaryl($C_1$–$C_5$) alkylpiperazino and either $R^3$ or $R^4$ is not hydrogen or both $R^3$ and $R^4$ are not hydrogen.

Specific preferred compounds of formula I include the following:

2-(R)-N-Hydroxy-2-[(4-methoxybenzenesulfonyl)(3-morpholin-4-yl-3-oxopropyl)amino]-3methylbutyramide;

2-(R)-2-[(2-Benzylcarbamoylethyl)(4-methoxybenzenesulfonyl)amino]-N-hydroxy-3-methylbutyramide;

2-(R)-N-Hydroxy-2-((4-methoxybenzenesulfonyl)(2-[(pyridin-3-ylmethyl)-carbamoyl]ethyl)amino)-3-methylbutyramide;

2-(R)-N-Hydroxy-2([4-methoxybenzenesulfonly][2-(methylpyridin-3-ylmethylcarbamoyl)ethyl]amino)-3-methylbutyramide;

4-(3-[1-(R)-1-Hydroxycarbamoyl-2-methylpropyl](4-methoxybenzene-sulfonyl)amino]propionyl)piperazine-1-carboxylic acid, tert-butyl ester;

2-(R)-N-Hydroxy-2-[(4-methoxybenzenesulfonyl)(3-oxo-3-piperazin-1-ylpropyl)amino)-3-methylbutyramide hydrochloride;

2-(R)-2-[(Benzylcarbamoylmethyl)(4-methoxybenzenesulfonyl)amino]N-hydroxy-3-methylbutyramide;

2-(R)-N-Hydroxy-2-([4methoxybenzenesulfonyl]-[(2-morpholin-4-ylethyl-carbamoyl)methyl]amino)-3-methylbutyramide; and 2-(R)-N-Hydroxy-2-((4-methoxybenzenesulfonyl)([(pyridin-3-ylmethyl)carbamoyl]methyl)amino)-3-methylbutyramide.

Other specific compounds of formula I include the following:

2-(R)-3,3,3-Trifluoro-N-hydroxy-2-[(methoxybenzenesulfonyl)(3-morpholin-4-yl-3-oxopropyl)amino]propionamide;

2-(R)-N-Hydroxy-2-((4-phenoxybenzenesulfonyl)[2-(methylpyridin-4-ylmethylcarbamoyl)ether]amino)-3-methylbutyramide;

4-[4-Methoxybenzenesulfonyl)(3-morpholin-4-yl-3-oxopropyl)amino]-1-methylpiperidene-4-carboxylic acid hydroxyamide;

2-(R)-N-Hydroxy-2-((4-methoxybenzenesulfonyl)-[3-(4-methylpiperazin-2-yl)-3-oxopropyl]amino)-3-methylbutyramide;

2-(R)-2-[(2-Carboxyethyl)(4-methoxybenzenesulfonyl) amino]-N-hydroxy-3-methylbutyramide;

[(2-Carboxyethyl)(3,4-dimethoxybenzenesulfonyl)amino]-N-hydroxy-acetamide 2-(R)-2[(2-Carbamoylethyl)(4-methoxybenzenesulfonyl) amino]-N-hydroxy-3-methylbutyramide 2-(R),3-(R)-3,N-Dihydroxy-2-[(4-methoxybenzenesulfonyl)(3-oxo-3-piperidin-1-ylpropyl) amino]-butyramide 2-(R)-N-Hydroxy-2-((4-methoxybenzenesulfonyl)[3-(methylpyridin-3-ylmethylcarbamoyl)propyl]amino)-3-methylbutyramide 2-(R)-N-Hydroxy-2-((4-methoxybenzenesulfonyl)[2-(methylcarboxymethylcarbamoyl)ethyl]amino)-3-methylbutyramide 2-(R)-N-Hydroxy-2-((4-methoxybenzenesulfonyl)-[(1-methylpiperidin-4-ylcarbamoyl)methyl]amino)-3-methylbutyramidecyclo 2-(R)-2-Cyclohexyl-N-hydroxy-2-((4-methoxybenzenesulfonyl)-[3-(4-methylpiperazin-1-yl)-3-oxopropyl]amino)-acetamide 2-(R)-N-Hydroxy-2-[(methoxybenzenesulfonyl)(3-morpholin-4-yl-3-oxopropyl)amino]-4-(morpholin-4-yl) butyramide.

The present invention also relates to a pharmaceutical composition for (a) the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of claim 1 or a pharmaceutically acceptable salt thereof, effective in such treatments and a pharmaceutically acceptable carrier.

The present invention also relates to a method for the inhibition of (a) matrix metalloproteinases or (b) the production of tumor necrosis factor (TNF) in a mammal, including a human, comprising administering to said mammal an effective amount of a compound of claim 1 or a pharmaceutically acceptable salt thereof.

The present invention also relates to a method for treating a condition selected from the group consisting of arthritis, cancer, tissue ulceration, restenosis, periodontal disease, epidermolysis, bullosa, scleritis and other diseases characterized by matrix metalloproteinase activity, AIDS, sepsis, septic shock and other diseases involving the production of tumor necrosis factor (TNF) in a mammal, including a human, comprising administering to said mammal an amount of a compound of claim 1 or a pharmaceutically acceptable salt thereof, effective in treating such a condition.

DETAILED DESCRIPTION OF THE INVENTION

The following reaction Schemes illustrate the preparation of the compounds of the present invention. Unless otherwise indicated $R^1$, $R^2$, $R^3$, $R^4$, n and Ar in the reaction Schemes and the discussion that follow are defined as above.

Scheme 1

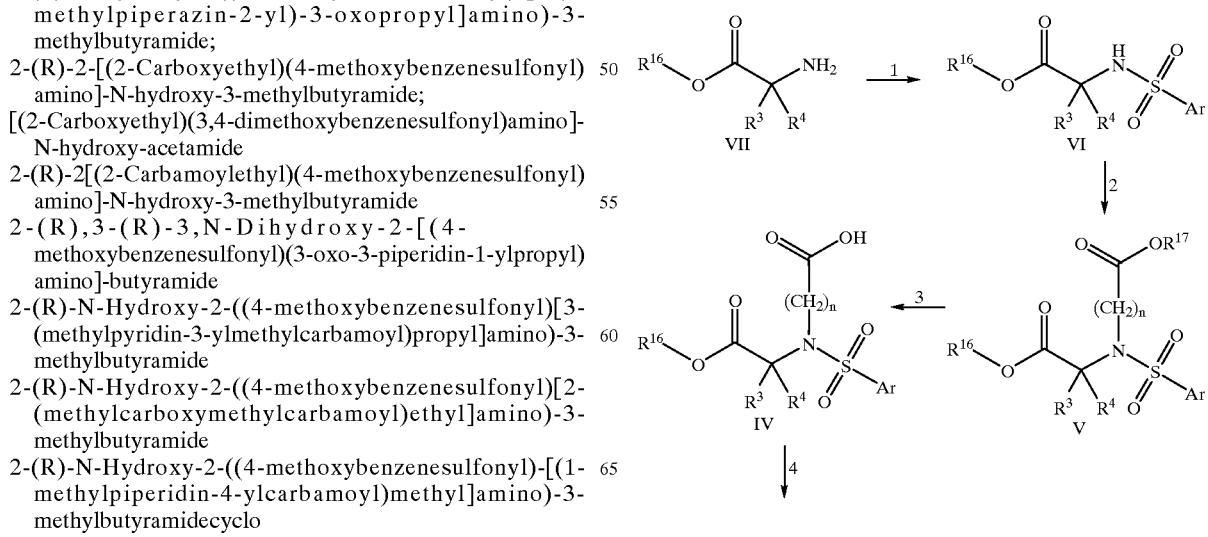

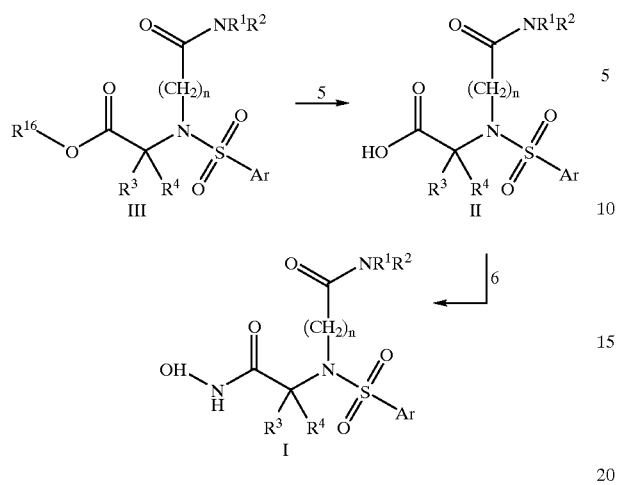
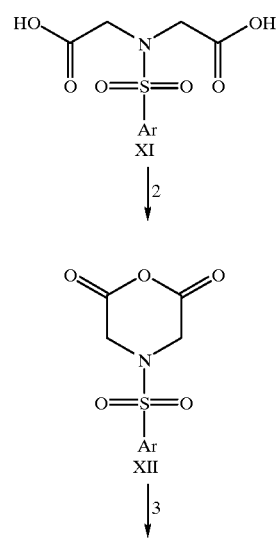
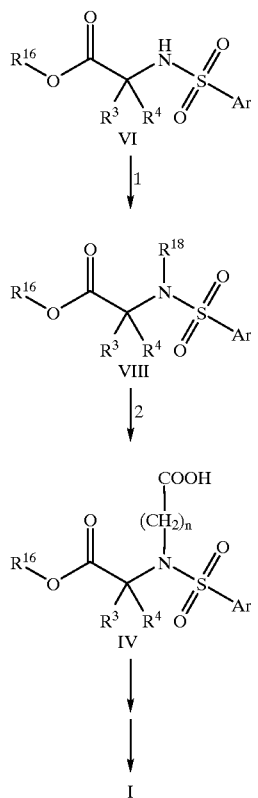
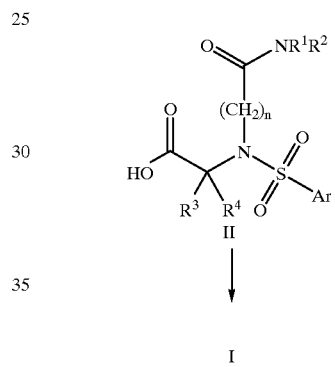
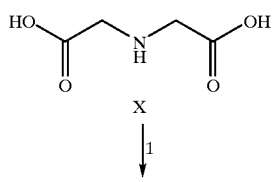

-continued

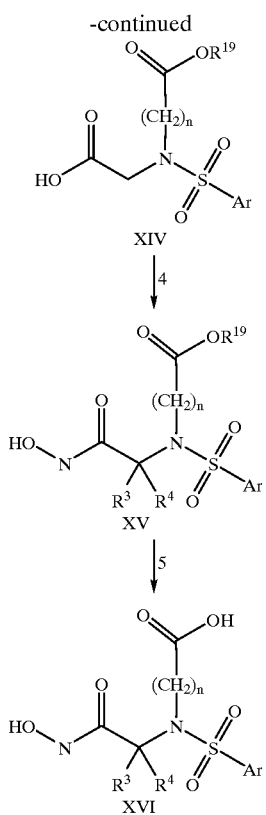

In reaction 1 of Scheme 1, the amino acid compound of formula VII, wherein $R^{15}$ is $(C_1-C_6)$alkyl, benzyl, allyl or tert-butyl, is converted to the corresponding compound of formula VI by reacting VII with a reactive functional derivative of an arylsulfonic acid compound, such as an arylsulfonyl chloride, in the presence of a base, such as triethylamine, and a polar solvent, such as tetrahydrofuran, dioxane, water or acetonitrile, preferably a mixture of dioxane and water. The reaction mixture is stirred, at room temperature, for a time period between about 10 minutes to about 24 hours, preferably about 60 minutes.

In reaction 2 of Scheme 1, the arylsulfonyl amino compound of formula VI, wherein $R^{18}$ is $(C_1-C_6)$alkyl, benzyl, allyl or tert-butyl, is converted to the corresponding compound of formula V, wherein n is 1, 3, 4, 5 or 6, by reacting VI with a reactive derivative of an alcohol of the formula.

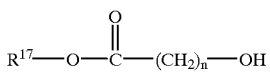

such as the chloride, bromide or iodide derivative, preferably the bromide derivative, wherein the $R^{17}$ protecting group is $(C_1-C_6)$alkyl, benzyl, allyl or tert-butyl, in the presence of a base such as potassium carbonate or sodium hydride, preferably sodium hydride, and a polar solvent, such as dimethylformamide. The reaction mixture is stirred, at room temperature, for a time period between about 60 minutes to about 48 hours, preferably about 18 hours. The $R^{17}$ protecting group is chosen such that it may be selectively removed in the presence of and without loss of the $R^{16}$ protecting group, therefore, $R^{17}$ cannot be the same as $R^{16}$. Removal of the $R^{17}$ protecting group from the compound of formula V to give the corresponding carboxylic acid of formula IV, in reaction 3 of Scheme 1, is carried out under conditions appropriate for that particular $R^{17}$ protecting group in use which will not affect the $R^{16}$ protecting group. Such conditions include; (a) saponification where $R^{17}$ is $(C_1-C_6)$alkyl and $R^{16}$ is tert-butyl, (b) hydrogenolysis where $R^{17}$ is benzyl and $R^{16}$ is tert-butyl or $(C_1-C_6)$alkyl, (c) treatment with a strong acid such as trifluoroacetic acid or hydrochloric acid where $R^{17}$ is tert-butyl and $R^{16}$ is $(C_1-C_6)$alkyl, benzyl or allyl, or (d) treatment with tributyltinhydride and acetic acid in the presence of catalytic bis(triphenylphosphine) palladium (II) chloride where $R^{17}$ is allyl and $R^{16}$ is $(C_1-C_6)$alkyl, benzyl of tert-butyl.

In reaction 4 of Scheme 1, the carboxylic acid of formula IV is condensed with an amine, $R^1R^2NH$, or the salt thereof, to give the corresponding amide compound of formula III. The formation of amides from primary or secondary amines or ammonia and carboxylic acids is achieved by conversion of the carboxylic acid to an activated functional derivative which subsequently undergoes reaction with a primary or secondary amine or ammonia to form the amide. The activated functional derivative may be isolated prior to reaction with the primary or secondary amine or ammonia. Alternatively, the carboxylic acid may be treated with oxalyl chloride or thionyl chloride, neat or in an inert solvent, such as chloroform, at a temperature between about 25° C. to about 80° C., preferably about 50° C., to give the corresponding acid chloride functional derivative. The inert solvent and any remaining oxalyl chloride or thionyl chloride is then removed by evaporation under vacuum. The remaining acid chloride functional derivative is then reacted with the primary or secondary amine or ammonia in an inert solvent, such as methylene chloride, to form the amide. The preferred method for the condenation of the carboxylic acid of formula IV with an amine to provide the corresponding amide compound of formula III is the treatment of IV with (benzotriazol-1-yloxy)tris(dimethylamino) phosphonium hexafluorophosphate in the presence of a base, such as triethylamine, to provide the benzotriazol-1-oxy ester in situ which, in turn, reacts with the amine, $R^1R^2N$, in an inert solvent, such as methylene chloride, at room temperature to give the amide compound of formula III.

Removal of the $R^{16}$ protecting group from the compound of formula III to give the corresponding carboxylic acid of formula II, in reaction 5 of Scheme 1, is carried out under conditions appropriate for the particular $R^{16}$ protecting group in use. Such conditions include; (a) saponification where $R^{16}$ is lower alkyl, (b) hydrogenolysis where $R^{16}$ is benzyl, (c) treatment with a strong acid, such as trifluoroacetic acid or hydrochloric acid, where $R^{16}$ is tert-butyl, or (d) treatment with tributyltinhydride and acetic acid in the presence of catalytic bis(triphenylphosphine) palladium (II) chloride where $R^{16}$ is allyl.

In reaction 6 of Scheme 1, the carboxylic acid compound of formula II is converted to the hydroxamic acid compound of formula I by treating II with 1-(3-dimethylaminopropyl) 3-ethylcarbodiimide and 1-hydroxybenztriazole in a polar solvent, such as dimethylformamide, followed by the action of hydroxylamine to the reaction mixture after a time period between about 15 minutes to about 1 hour, preferably about 30 minutes. The hydroxylamine is preferably generated in situ from a salt form, such as hydroxylamine hydrochloride, in the presence of a base, such as N-methylmorpholine. Alternatively, a protected derivative of hydroxylamine or its salt form, where the hydroxyl group is protected as a tert-butyl, benzyl or allyl ether, may be used in the presence of (benzotriazol-1-yloxy)tris(dimethylamino) phosphonium hexafluorphosphate and a base, such as N-methylmorpholine. Removal of the hydroxylamine protecting group is carried out by hydrogenolysis for a benzyl protecting group or treatment with a strong acid, such as trifluoroacetic acid, for a tert-butyl protecting group. The allyl protecting group may be removed by treatment with tributyltinhydride and acetic acid in the presence of catalytic bis(triphenylphosphine) palladium (II) chloride. N,O-bis(4-methoxybenzyl)hydroxylamine may also be used as the protected hydroxylamine derivative where deprotection is achieved using a mixture of methanesulfonic acid and trifluoroacetic acid.

In reaction 1 of Scheme 2, the arylsulfonylamino compound of formula VI, wherein $R^{16}$ is $(C_1-C_6)$alkyl, benzyl or tert-butyl, is converted to the corresponding compound of formula VIII, wherein $R^{18}$ is 2-propenyl or 3-butenyl, by reacting IX with a reactive functional derivative, such as the halide, preferably the iodide derivative, of 2-propen-1-ol when $R^{18}$ is 2-propenyl or 3-buten-1-ol when $R^{18}$ is 3-butenyl, in the presence of a base, such as potassium carbonate, cesium carbonate or sodium hydride, preferably sodium hydride when $R^{18}$ is 2-propenyl or cesium carbonate when $R^{18}$ is 3-butenyl. The reaction is stirred in a polar solvent, such as dimethylformamide, at room temperature, for a time period between about 2 hours to about 48 hours, preferably about 18 hours.

In reaction 2 of Scheme 2, the compound of formula VIII is converted to the carboxylic acid compound of formula IV, wherein n is 2. The compound of formula VIII, wherein $R^{18}$ is 2-propenyl, is converted to the compound of formula IV, wherein n is 2, by reacting VIII with borane-dimethylsulfide complex, followed by immediate oxidation using chromium trioxide in aqueous acetic acid. The oxidative cleavage of terminal olefins to carboxylic acids can be achieved by several methods known in the art. The preferred method for the oxidative cleavage of the compound of formula VIII, wherein $R^{18}$ is 3-butenyl, to obtain the carboxylic acid compound of formula IV is to react VIII with sodium periodate in the presence of a catalytic amount of ruthenium (III) chloride in a mixture of carbon tetrachloride, acetonitrile and water.

The compound of formula IV, wherein n is 2, is further reacted to provide the hydroxamic acid compound of formula I, wherein n is 2, according to the procedure described above in reactions 4, 5 and 6 of Scheme 1.

An alternative method for the synthesis of the hydroxamic acid compound of formula I, wherein n is 1 and $R^3$ and $R^4$ are both hydrogen, is shown in reaction 1 of Scheme 3, beginning with reacting iminoacetic acid or a metal or ammonium salt of iminoacetic acid of formula X with a functional derivative of an arylsulfonic acid compound, such as an arylsulfonyl chloride, at room temperature, in the presence of a suitable base, such as triethylamine, and a polar solvent such as tetrahydrofuran, dioxane, water or acetonitrile, preferably a mixture of dioxane and water, to give the corresponding dicarboxylic acid compound of formula XI.

In reaction 2 of Scheme 3, the dicarboxylic acid compound of formula XI is dehydrated to give a cyclic anhydride compound of formula XII. The formation of cyclic anhydrides by dehydration of dicarboxylic acids may be achieved by a variety of means. The preferred method for the dehydration of the dicarboxylic acid compound of formula XI to give a cyclic anhydride compound of formula XII is to treat XI with an excess of acetic anhydride at a temperature between about 25° C. to about 80° C., preferably about 60° C. Excess acetic anhydride and acetic acid, a by-product of the reaction, are removed by evaporation under reduced pressure leaving the cyclic anhydride compound of formula XII.

In reaction 3 of Scheme 3, the cyclic anhydride compound of formula XII is reacted, at room temperature, with an amine, $NR^1R^2$, or a salt of the amine, such as the hydrochloride, in the presence of a base, such as triethylamine, to give the carboxylic acid of formula II, wherein n is 1 and $R^3$ and $R^4$ are both hydrogen. Suitable solvents for the reaction are those that will not react with the starting materials, which include chloroform, methylene chloride and dimethylformamide, preferably methylene chloride.

The compound of formula II is further reacted to give the hydroxamic acid compound of formula I, wherein n is 1 and $R^3$ and $R^4$ are both hydrogen, according to the procedure described above in reaction 6 of Scheme 1.

In reaction 1 of Scheme 4, the carboxylic acid compound of formula IV, wherein n is 2, is converted to the corresponding compound of formula V, wherein $R^{19}$ is $(C_1-C_6)$ alkyl or tert-butyl, by reacting IV with a compound of the formula

$(R^{19}O)_2CHN(CH_3)_2$ wherein $R^{19}$ is $(C_1-C_6)$alkyl or tert-butyl, in an inert solvent, such as toluene, at a temperature between about 60° C. to about 100° C., for a time period between about 1 hour to about 3 hours, preferably 2hours. In reaction 2 of Scheme 4, the arylsulfonyl amino compound of formula VI wherein n is 1, 3, 4, 5 or 6 and $R^{16}$ is $(C_1-C_6)$alkyl, benzyl, allyl or tert-butyl, is converted to the corresponding compound of formula XIII, wherein $R^{19}$ is $(C_1-C_8)$alkyl or tert-butyl, by reacting VI with a reactive derivative of an alcohol of the formula

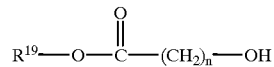

such as the chloride, bromide or iodide derivative, preferably the bromide derivative, wherein $R^{19}$ is $(C_1-C_8)$alkyl or tert-butyl, in the presence of a base such as potassium carbonate or sodium hydride, preferably sodium hydride, and a polar solvent, such as dimethylformamide. The reaction is stirred, at room temperature, for a time period between about 60 minutes to about 48 hours, preferably about 18 hours. The $R^{16}$ protecting group, of the compounds of formulas IV and VI, is chosen such that it may be selectively removed in the presence of and without loss of the $R^{19}$ $(C_1-C_6)$alkyl or tert-butyl group, therefore, $R^{16}$ cannot be the same as $R^{19}$. Removal of the $R^{16}$ protecting group from the compound of formula XIII to give the corresponding carboxylic acid of formula XIV, wherein n is 1 to 6, in reaction 3 of Scheme 4, is carried out under conditions appropriate for that particular $R^{16}$ protecting group in use which will not affect the $R^{19}$ $(C_1-C_6)$alkyl or tert-butyl group,. Such conditions include; (a) saponification where $R^{16}$ is $(C_1-C_6)$alkyl and $R^{19}$ is tert-butyl, (b) hydrogenolysis where $R^{18}$ is benzyl and $R^{19}$ is tert-butyl or $(C_1-C_6)$alkyl, (c) treatment with a strong acid such as trifluoroacetic acid or hydrochloric acid where $R^{16}$ is tert-butyl and $R^{19}$ is $(C_1-C_6)$alkyl, or (d) treatment with tributyltinhydride and acetic acid in the presence of catalytic bis(triphenylphosphine) palladium (II) chloride where $R^{16}$ is allyl and $R^{19}$ is $(C_1-C_6)$alkyl or tert-butyl.

In reaction 4 of Scheme 4, the carboxylic acid of formula XIV is converted to the to the hydroxamic acid compound of formula XV, wherein n is 1 to 6, by treating XIV with 1-(3-dimethylaminopropyl)-3-ethylcarbodiimide and 1-hydroxybenztriazole in a polar solvent, such as dimethylformamide, followed by the addition of hydroxylamine to the reaction mixture after a time period between about 15 minutes to about 1 hour, preferably about 30 minutes. The hydroxylamine is preferably generated in situ from a salt form, such as hydroxylamine hydrochloride, in the presence of a base, such as N-methylmorpholine. Alternatively, a protected derivative of hydroxylamine or its salt form, where the hydroxyl group is protected as a tert-butyl, benzyl or allyl ether, may be used in the presence of (benzotriazol-1-yloxy)tris(dimethylamino) phosphonium hexafluorophosphate and a base, such as N-methylmorpholine. Removal of the hydroxylamine protecting groups is carried out by hydrogenolysis for a benzyl protecting group or treatment with a strong acid, such as trifluoroacetic acid, for a tert-butyl protecting group. The allyl protecting group may be removed by treatment with tributyltinhydride and acetic acid in the presence of catalytic bis(triphenylphosphine) palladium (II) chloride. N,O-bis(4-methoxybenzyl)hydroxylamine may also be used, when $R^{19}$ is ($C_1$—$C_6$)alkyl, as the protected hydroxylamine derivative where deprotection is achieved using a mixture of methanesulfonic acid and trifluoroacetic acid.

In reaction 5 of Scheme 4, the amide formula of formula XV is, if desired, converted to the corresponding carboxylic acid compound of formula XVI by (a) saponification where $R^{19}$ is lower alkyl or (b) treatment with a strong acid, such as trifluoroacetic acid or hydrochloric acid, where $R^{19}$ is tert-butyl.

Pharmaceutically acceptable salts of the acid compounds of the invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymetyl)-methylammonium slats.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure The ability of the compounds of formula I or their pharmaceutically acceptable salts (hereinafter also referred to as the compounds of the present invention) to inhibit matrix metalloproteinases or the production of tumor necrosis factor (TNF) and, consequently, demonstrate their effectiveness for treating diseases characterized by matrix metalloproteinase or the production of tumor necrosis factor is shown by the following in vitro assay tests.

BIOLOGICAL ASSAY

Inhibition of Human Collagenase (MMP-1)

Human recombinant collagenase is activated with trypsin using the following ratio: 10 µg trypsin per 100 µg of collagenase. The trypsin and collagenase are incubated at room temperature for 10 minutes then a five fold excess (50 µg/10 µg trypsin) of soybean trypsin inhibitor is added.

10 mM stock solutions of inhibitors are made up in dimethyl sulfoxide and then diluted using the following Scheme:

10 mM→120 µM→12 µM→1.2 µM→0.12 µM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25 µl is then added to appropriate wells of the microfluor plate. Final concentration of collagenase in the assay is 100 ng/ml.

Substrate (DNP-Pro-Cha-Gly-Cys(Me)-His-Ala-Lys (NMA)-$NH_2$) is made as a 5 mM stock in dimethyl sulfoxide and then diluted to 20 µM in assay buffer. The assay is initiated by the addition of 50 µl substrate per well of the microfluor plate to give a final concentration of 10 µM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minutes data. Data is plotted as inhibitor concentration vs % control (inhibitor fluorescence divided by fluorescence of collagenase alone×100). $IC_{50}$'s are determined from the concentration of inhibitor that gives a signal that is 50% of the control.

If $IC_{50}$'s are reported to be <0.03 µM then the inhibitors are assayed at concentrations of 0.3 µM, 0.03 µM, 0.03 µM and 0.003 µM.

Inhibition of Gelatinase (MMP-2)

Inhibition of gelatinase activity is assayed using the Dnp-Pro-Cha-Gly-Cys(Me)-His-Ala-Lys(NMA)-$NH_2$ substrate (10 µM) under the same conditions as inhibition of human collagenase (MMP-1).

72 kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 µM, 3 µM, 0.3 µM and 0.03 µM. Each concentration is done in triplicate.

Fluorescence readings (360 nm excitation, 460 emission) are taken at time zero and then at 20 minutes intervals for 4 hours.

$IC_{50}$'s are determined as per inhibition of human collagenase (MMP-1) If $IC_{50}$'s are reported to be less than 0.03 µM, then the inhibitors are assayed at final concentrations of 0.3 µM, 0.03 µM, 0.003 µM and 0.003 µM.

Inhibition of Stromelysin Activity (MMP-3)

Inhibition of stromelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[$CH_2CH(CH_3)_2$]CO-Leu-Gly-$OC_2H_5$] yields a mercaptan fragment that can be monitored in the presence of Ellman's reagent.

Human recombinant prostromelysin is activated with trypsin using a ratio of 1 µl of a 10 mg/ml trypsin stock per 28 µg of stromelysin. The trypsin and stromelysin are incubated at 37° C. for 15 minutes followed by 10 µl of 10 mg/ml soybean trypsin inhibitor for 10 minutes at 37° C. for 10 minutes at 37° C. to quench trypsin activity.

Assays are conducted in a total volume of 250 μl of assay buffer (200 mM sodium chloride, 50 mM MES, and 10 mM calcium chloride, pH 6.0) in 96-well microliter plates. Activated stromelysin is diluted in assay buffer to 25 μg/ml. Ellman's reagent (3-Carboxy-4-nitrophenyl disulfide) is made as a 1M stock in dimethyl formamide and diluted to 5 mM in assay buffer with 50 μl per well yielding at 1 mM final concentration.

10 mM stock solutions of inhibitors are made in dimethyl sulfoxide and diluted serially in assay buffer such that addition of 50 μL to the appropriate wells yields final concentrations of 3 μM, 0.3 μM, 0.003 μM, and 0.0003 μM. All conditions are completed in triplicate.

A 300 mM dimethyl sulfoxide stock solution of the peptide substrate is diluted to 15 mM in assay buffer and the assay is initiated by addition of 50 μl to each well to give a final concentration of 3 mM substrate. Blanks consist of the peptide substrate and Ellman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 μM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 μM, 3 μM, 0.3 μM, and 0.03 μM.

Substrate (Dnp-Pro-Cha-Gly-Cys(Me)-His-Ala-Lys(NMA)-$NH_2$) is prepared as for inhibition of human collagenase (MMP-1) and 50 μl is added to each well to give a final assay concentration of 10 μM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 μM, inhibitors are then assayed at final concentrations of 0.3 μM, 0.03 μM, 0.003 μM and 0.0003 μM.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anti-coagulated human blood using a one-step FicoII-hypaque separation technique. (2) The mononuclear cells were washed three times in Hanks balanced salt solution (HBSS) with divalent cations and resuspended to a density of $2\times10^5$/ml in HBSS containing 1% BSA. Differential counts determined using the Abbott Cell Dyn 3500 analyzer indicated that monocytes ranged from 17 to 24% of the total cells in these preparations.

180μ of the cell suspension was aliquoted into flate bottom 96 well plates (Costar). Additions of compounds and LPS (100 ng/ml final concentration) gave a final volume of 200 μl. All conditions were performed in triplicate. After a four hour incubation at 37° C. in an humidified $CO_2$ incubator, plates were removed and centrifuged (10 minutes at approximately 250×g) and the supernatants removed and assayed for TNFα using the R&D ELISA Kit.

For administration to humans for the inhibition of matrix metalloproteinases or the production of tumor necrosis factor (TNF), a variety of conventional routes may be used including orally, parenterally and typically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like a polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oil solutions are suitable for intraarticular, intramuscular and subcutaneous injection purposes. The preparation of all these solutions under sterile conditions is readily accomplished by standard pharmaceutical techniques well known to those skilled in the art.

The present invention is illustrated by the following examples, but it is not limited to the details thereof.

EXAMPLE 1

2-(R)-N-Hydroxy-2-[(-methoxybenzenesulfonyl)(2-morpholin-4-yl-2-oxoethyl)amino]-3-methylbutyramide To a solution of D-valine benzyl ester hydrochloride (2.4 grams, 10 mmol) and triethylamine (2.5 grams, 3.5 mL, 25 mmol) in water (50 mL) and 1,4-dioxane (50 mL) is added 4-methoxybenzenesulfonyl chloride (2.3 grams, 11 mmol). The mixture was stirred at room temperature for 1 hour and then most of the solvent was removed by evaporation under vacuum. The mixture was diluted with ethyl acetate and was washed successively with dilute hydrochloric acid solution, water and brine. The organic solution was dried over magnesium sulfate and concentrated to leave N-(4-methoxybenzenesulfonyl)-D-valine benzyl ester as a white solid, 3.6 grams (97%); m.p. 92–94° C.

N-(4-Methoxybenzenesulfonyl)-D-valine benzyl ester (1.50 grams, 4.0 mmol) was added to a suspension of sodium hydride (0.1 grams, 4.2 mmol) in dry dimethylformamide (20 mL) and, after 30 minutes, tert-butyl bromoacetate (0.8 mL, 4.2 mmol) was added. The resulting mixture was stirred overnight at room temperature and was then quenched by addition of saturated ammonium chloride solution (3 mL). The dimethylformamide was removed by evaporation under vacuum. The residue was taken up in ethyl acetate and washed with water and brine. After drying over magnesium sulfate, ethyl acetate was evaporated to leave an oil from which 2-(R)-2-[tert-butoxycarbonylmethyl (4-methoxybenzenesulfonyl)amino]-3-methylbutyric acid benzyl ester, a clear oil (1.92 grams, 98%), was isolated using flash chromatography on silica gel eluting with 15% ethyl acetate in hexane.

To a cold (0° C.) solution of 2-(R)-2-[tert-butoxycarbonylmethyl(4-methoxybenzenesulfonyl)amino]-3-methylbutyric acid benzyl ester (1.92 grams, 3.9 mmol) in methylene chloride (28 mL) was added trifluoroacetic acid (7 mL). The resulting solution was allowed to warm to room temperature and was stirred overnight. The methylene chloride and trifluoroacetic acid were evaporated under vacuum leaving 2-(R)-2-[carboxymethyl(4-methoxybenzenesulfonyl)amino)]-3-methylbutyric acid benzyl ester as a clear oil, 1.70 grams (100%).

To a solution of 2-(R)-2-[carboxymethyl(4-methoxybenzenesulfonyl)amino]-3-methylbutyric acid benzyl ester (573 mg, 1.32 mmol) in methylene chloride (12 mL) were added sequentially triethylamine (0.46 mL, 3.28 mmol), morpholine (0.127 mL, 1.46 mmol) and (benzotriazol-1-yloxy)tris(dimethylamino)phosphonium hexafluorophosphate (646 mg, 1.46 mmol). The mixture was stirred at room temperature overnight and then diluted with ethyl acetate. The solution was washed with 0.5 N hydrochloric acid solution and brine, dried over magnesium sulfate and concentrated under vacuum. The residue was chromatographed on silica gel using 40% ethyl acetate in hexane affording 2-(R)-2-[(4-methoxybenzenesulfonyl)(2-morpholin-4-yl-oxoethyl)amino]-3-methylbutyric acid benzyl ester as a clear oil, 590 mg (89%).

To a solution of 2-(R)-2-[(4-methoxybenzenesulfonyl)(2-morpholin-4-yl-2-oxoethyl)amino]-3-methylbutyric acid benzyl ester (590 mg, 1.17 mmol) in ethanol (50 mL) was added 10% palladium on activated carbon (200 mg). The mixture was agitated under 3 atmospheres hydrogen in a Parr shaker for 2 hours. The catalyst was removed by filtration through nylon (pore size 0.45 µm) and the solvent was evaporated leaving 2-(R)-2-[(4-methoxybenzenesulfonyl)(2-morpholin-4-yl-2-oxoethyl) amino]-3-methylbutyric acid as a white foam, 485 mg (100%).

To a solution of 2-(R)-2-[(4-methoxybenzenesulfonyl)(2-morpholin-4-yl-2-oxoethyl)amino]-3-methylbutyric acid (485 mg, 1.17 mmol) in methylene chloride (12 mL) were added sequentially triethylamine (0.52 mL, 3.71 mmol), O-benzylhydroxylamine hydrochloride (205 mg, 1.28 mmol) and benzotriazol-1-yloxy)tris(dimethylamino) phosphonium hexafluorophosphate (570 mg, 1.29 mmol). The mixture was stirred at room temperature overnight and then diluted with ethyl acetate. The solution was washed sequentially with 0.5 N hydrochloric acid solution, water, saturated sodium hydrogen carbonate solution and brine, dried over magnesium sulfate and concentrated under vacuum. The residue was chromatographed on silica gel using 20% hexane in ethyl acetate to afford 2-(R)-N-benzyloxy-2-[(4-methoxybenzenesulfonyl)(2-morpholin-4-yl-2-oxoethyl)amino]-3-methylbutyramide as a white foam, 510 mg (84%).

To a solution of 2-(R)-N-benzyloxy-2-[(4-methoxybenzenesulfonyl)(2-morpholin-4-yl-2-oxoethyl) amino]-3-methylbutyramide (510 mg, 0.98 mmol) in methanol (50 mL) was added 5% palladium on activated carbon (120 mg). The mixture was agitated under 2 atmospheres hydrogen in a Parr shaker for 2 hours. The catalyst was removed by filtration through nylon (pore size 0.45 µm) and the solvent was evaporated leaving 2-(R)-N-hydroxy-2-[(-methoxybenzenesulfonyl)(2-morpholin-4-yl-2-oxoethyl) amino]-3-methylbutyramide as a white solid, 418 mg (99%); $^1$H NMR (CDCl$_3$): δ 10.3 (br s, 1H), 7.90 (br s, 1 H, overlapped), 7.86 (d, J=8.8 Hz, 2H, overlapped), 6.94 (d, J=8.8 Hz, 2H), 4.39 (d, J=17.1 Hz, 1H), 4.09 (d, J=17.1, 1H), 3.84 (s, 3H), 3.80–3.48 (m, 9H), 2.20–1.95 (m, 1H), 0.82 (d, J=6.5 Hz, 3H), 0.45 (d, J=6.5 Hz, 3H); MS (LSIMS): m/z 430 (M+H).

EXAMPLE 2

2-(R)-N-Hydroxy-2-[(4-methoxybenzenesulfonyl)(3-morpholin-4-yl-3-oxopropyl)amino]-3-methylbutyramide To a solution of N-(4-methoxybenzenesulfonyl)-D-valine benzyl ester (2.2 grams, 5.83 mmol) in dry dimethylformamide (40 mL) were added cesium carbonate (2.3 grams, 7.1 mmol) and 1-iodo-3-butene (1.3 grams, 7.1 mmol). The mixture was stirred at room temperature overnight and was then poured into water. The mixture was extracted twice with ether and the combined ether extracts were washed with brine, dried over magnesium sulfate and concentrated under reduced pressure. The residue was taken up in 20% ethyl acetate/hexane; starting material N-(4-methoxybenzenesulfonyl)-D-valine benzyl ester (1.5 g) crystallized from the mixture and was recovered by filtration. The filtrate was concentrated under vacuum and the residue was chromatographed on silica gel using 20% ethyl acetate/hexane as eluant to provide 2-(R)-2-[but-3-enyl(4-methoxybenzenesulfonyl)amino]-3-methylbutyric acid benzyl ester as a clear oil, 404 mg (16%).

To a mixture of 2-(R)-2-[but-3-enyl(4-methoxybenzenesulfonyl)amino]-3-methylbutyric acid benzyl ester (780 mg, 1.81 mmol) and ruthenium (III) chloride hydrate (10 mg, 0.048 mmol) in acetonitrile (6 mL), carbon tetrachloride (6 mL) and water (8 mL) was added sodium periodate (1.7 grams, 7.9 mmol). After stirring at room temperature for 2 hours, the mixture was diluted with methylene chloride and filtered through diatomaceous earth. The organic layer was separated, washed with dilute hydrochloric acid solution and brine, dried over magnesium sulfate and concentrated to leave 2-(R)-2-[2-carboxyethyl (4-methoxybenzenesulfonyl)amino]-3-methylbutyric acid benzyl ester as an oil, 710 mg (87%).

Alternatively, the intermediate 2-(R)-2-[2-carboxyethyl (4-methoxybenezenesulfonyl)amino]-3-methylbutyric acid benzyl ester was prepared by the following higher yielding procedure:

N-(4-Methoxybenzenesulfonyl)-D-valine benzyl ester (18.8 grams, 49.8 mmol) was added to a suspension of sodium hydride (1.3 grams, 54 mmol) in dry dimethylformamide (200 mL) and, after 1.5 hours, a solution of allyl bromide (4.7 mL, 54 mmol) was added. The resulting mixture was stirred overnight at room temperature and was then quenched by addition of saturated ammonium chloride solution. The dimethylformamide was removed by evaporation under vacuum. The residue was taken up in ether and washed with water and brine. After drying over magnesium sulfate, ether was evaporated to leave an oil from which 2-(R)-2-[(4-methoxybenzenesulfonyl)prop-2-enylamino]-3-methylbutyric acid benzyl ester, a clear oil (18.1 grams, 87%), was isolated using flash chromatography on silica gel eluting with 10% ethyl acetate in hexane and then 20% ethyl acetate in hexane.

To a 1 M solution of borane/disulfide complex in methylene chloride (1.45 mL, 2.9 mmol) was added a solution of 2-(R)-2-[(4-methoxybenzenesulfonyl)prop-2-enylamino]-3-methylbutyric acid benzyl ester (3.6 grams, 8.6 mmol) in methylene chloride (8 mL). The solution was stirred at room temperature for 4 hours at which time more 1 M solution of borane/disulfide complex in methylene chloride (2.0 mL, 4.0 mmol) was added. The mixture was stirred at room temperature overnight and was then added dropwise to a mechanically stirred solution of chromium trioxide (5.1 grams, 51.6 mole) in acetic acid (31 mL) and water (3.5 mL) while keeping the internal temperature between −5° C. and 10° C. After stirring at room temperature overnight, the mixture was diluted with water and extracted with methylene chloride. The extract was washed with brine, dried (magnesium sulfate) and concentrated. The residue was chromatographed on silica gel eluting successively with chloroform and 2% methanol in chloroform to afford 2-(R)-2-[2-carboxyethyl(4-methoxybenzenesulfonyl)amino]-3-methylbutyric acid benzyl as an oil (2.42 grams, 63%).

To a solution of 2-(R)-2-[2-carboxyethyl(4-methoxybenzenesulfonyl)amino]-3-methylbutyric acid benzyl ester (710 mg, 1.58 mmol) in methylene chloride (15 mL) were added sequentially triethylamine (0.47 mL, 3.35 mmol), morpholine (0.15 mL, 1.72 mmol)and(benzotriazol-1-yloxy)tris(dimethylamino)phosphoniumhexafluorophosphate (769 mg, 1.74 mmol). The mixture was stirred at room temperature overnight and then diluted with methylene chloride. The solution was washed with 0.5 N hydrochloric acid solution and brine, dried over magnesium sulfate and concentrated under vacuum. The solid residue was chromatographed on silica gel using 20% hexane in ethyl acetate affording 2-(R)-2-[(4-methoxybenzenesulfonyl)(3-morpholin-4-yl-3-oxopropyl) amino]-3-methylbutyric acid benzyl ester as a clear oil, 725 mg (88%).

To a solution of 2-(R)-2-[(4-methoxybenzenesulfonyl)(3-morpholin-4-yl-3-oxopropyl)amino]-3-methylbutyric acid benzyl ester (725 mg, 1.40 mmol) in ethanol (35 mL) was added 10% palladium on activated carbon (50 mg). The mixture was agitated under 3 atmospheres hydrogen in a Parr shaker for 3 hours. The catalyst was removed by filtration through nylon (pore size 0.45 μm) and the solvent was evaporated leaving 2-(R)-(2)-[(4-methoxybenzenesulfonyl)(3-morpholin-4-yl-3-oxopropyl)amino]-3-methylbutyric acid as a white solid, 540 mg (90%).

To a solution of 2-(R)-2-[(4-methoxybenzenesulfonyl)(3-morpholin-4-yl-3-oxopropyl)amino]-3-methylbutyric acid (540 mg, 1.26 mmol) and 1-hydroxybenztriazole hydrate (205 mg, 1.33 mmol) in dry dimethylformamide (12 mL) was added 1-(3-dimethylaminopropyl)-3-ethylcarbodiimide hydrochloride (289 mg, 1.51 mmol). After stirring for 30 minutes, hydroxylamine hydrochloride (350 mg, 5.04 mmol) and then triethylamine (1.0 mL, 7.17 mmol) were added. The mixture was stirred at room temperature overnight and then diluted with ethyl acetate. The solution was washed sequentially with water, 0.5 N hydrochloric acid solution and brine. The solution was then dried over magnesium sulfate and concentrated under vacuum to leave a white foam. The material was dissolved in toluene, filtered and concentrated. The residue was triturated with ether to afford 2-(R)-N-hydroxy-2-[(4-methoxybenzenesulfonyl)(3-morpholin-4-yl-3-oxopropyl)amino]-3-methylbutyramide as a solid, 200 mg (36%); $^1$H NMR (CDCl$_3$): δ 9.35 (br s, 1H), 7.73 (d, J=8.9 Hz, 2H), 6.95 (d, J=8.9 Hz, 2H), 3.86 (s, 3H), 3.83–3.73 (m, 1H), 3.70–3.52 (m, 7H), 3.46–3.43 (m, 2H), 3.41–3.29 (m, 1H), 2.92–2.69 (m, 2H), 2.30–2.17 (m, 1H), 0.84 (d, J=6.5 Hz, 3H), 0.41 (d, J=6.5 Hz, 3H); MS (particle beam): m/z 444 (M+H), 428, 383, 329; HRMS calculated for $C_{19}H_{30}N_3O_7S$ (M+H): 444.1804, Found: 464.1818.

The title compounds of Examples 3–6 were prepared by a method analogous to that described in Example 2 using (2-(R)-2-[2-carboxyethyl(4-methoxybenzenesulfonyl)amino]-3-methylbutyric acid benzyl ester as the starting material which is coupled with the amine indicated.

EXAMPLE 3

2-(R)-2-[(2-Benzylcarbamoylethyl)(4-methoxybenzenesulfonyl)amino]-N-hydroxy-3-methylbutyramide Coupled with benzylamine; $^1$H NMR (DMSO-d$_6$): δ10.72 (s, 1H), 8.89 (s, 1H), 8.39 (m, 1H), 7.74 (d, J=9.0 Hz, 2H), 7.32–7.21 (m, 5H), 7.05 (d, J=9.0 Hz, 2H), 4.21 (d, J=5.9 Hz, 2H), 4.02–3.87 (m, 1H), 3.82 (s, 3H), 3.63 (d, J=10.8 Hz, 1H), 3.29–3.17 (m, 1H), 2.71–2.57 (m, 1H), 2.52–2.40 (m, 1H), 2.06–1.94 (m, 1H), 0.77 (d, J=6.6 Hz, 3H), 0.74 (d, J=6.5 Hz, 3H); MS (LSIMS): m/z 464 (M+H); HRMS calculated for $C_{22}H_{30}N_3O_6S$ (M+H): 464.1855. Found: 464.1832.

EXAMPLE 4

2-(R)-N-Hydroxy-2-((4-methoxybenzenesulfonyl)(2-[(pyridin-3-ylmethyl)carbamoyl]ethyl)amino)-3-methylbutyramide Coupled with 3-pyridylmethylamine: $^1$H NMR (DMSO-d$_6$): δ 10.72 (s, 1H), 8.89 (s, 1H), 8.49–8.42 (m, 3H), 7.73 (d, J=8.9 Hz, 2H), 7.63–7.60 (m, 1H), 7.32 (dd, J=4.8, 7.8 Hz, 1H), 7.05 (d, J=8.9 Hz, 2H), 4.23 (d, J=5.8 Hz, 2H), 4.00–3.88 (m, 1H), 3.81 (s, 3H), 3.62 (d, J=10.8 Hz, 1H), 3.27–3.17 (m, 1H), 2.69–2.58 (m, 1H), 2.52–2.41 (m, 1H), 2.07–1.94 (m, 1H), 0.76 (d, J=6.5 Hz, 3H), 0.72 (d, J=6.4 Hz, 3H); MS (LSIMS): m/z 465 (M+H).

EXAMPLE 5

2-(R)-N-Hydroxy-2-([4-methoxybenzenesulfonyl][2-(methylpyridin-3-ylmethylcarbamoyl)ethyl]amino)-3-methylbutyramide Coupled with 3-(N-methylaminomethyl)pyridine: $^1$H NMR (DMSO-d$_6$): δ 10.75 (br s, 1H), 8.92 (s, 1H), 8.52–8.29 (m, 2H), 7.75 (d, J=8.8 Hz, 1.4H), 7.67 (d, J=8.8 Hz, 0.6H), 7.62–7.58 (m, 1H), 7.42–7.32 (m, 1H), 7.06 (d, J=8.8 Hz, 1.4H), 7.01 (d, J=8.8 Hz, 0.6H), 4.55–4.41 (m, 2H), 3.94–3.82 (m, 1H), 3.81 (s, 2.1H), 3.80 (s, 0.9H), 3.68–3.60 (m, 1H), 3.33–3.19 (m, 1H), 2.90–2.50 (m, 2H), 2.88 (s, 2.1H overlapped), 2.79 (s, 0.9H), 2.05–1.80 (m, 1H), 0.79–0.63 (m, 6H): MS (thermospray): m/z 479 (M+H), 364.

EXAMPLE 6

4-(3-[(1-(R)-1-Hydroxycarbamoyl-2-methylpropyl)(4-methoxybenzenesulfonyl)amino]propionyl)piperazine-1-carboxylic acid, tert-butyl ester Coupled with tert-butyl-1-piperazinecarboxylate: $^1$H NMR (DMSO-d$_6$): δ 10.77 (br s, 1H), 8.93 (s, 1H), 7.74 (d, J=8.9 Hz, 2H), 7.06 (d, J=8.9 Hz, 2H), 3.90–3.80 (m, 1H), 3.82 (s, 3H, overlapped), 3.64 (d, J=10.8 Hz, 1H), 3.60–3.16 (m, 9H), 2.80–2.71 (m, 1H), 2.59–2.47 (m, 1H), 2.03–1.91 (m, 1H), 1.39 (s, 9H), 0.77 (d, J=6.5 Hz, 3H), 0.71 (d, J=6.5, 3H); MS (thermospray): m/z 543 (M+H), 443, 382, 328.

EXAMPLE 7

2-(R)-N-Hydroxy-2-[(4-methoxybenzenesulfonyl)(3-oxo-3-piperazin-1-ylpropyl)amino]-3-methylbutyramide hydrochloride A solution of 4-(3-[(1-(R)-1-hydroxycarbamoyl-2-methylpropyl)(4-methoxybenzenesulfonyl)amino]propionyl)piperazine-1-carboxylic acid, tert-butyl ester [Example 6] (430 mg, 0.79 mmol) in methylene chloride (11 mL) was cooled to 0° C. Hydrogen chloride gas was then bubbled through the solution for about 0.5 minute. The solution was allowed to warm to room temperature with stirring over 1 hour. Volatiles were removed by evaporation and the residue was filtered, washing with methylene chloride to collect solid 2-(R)-N-hydroxy-2-[(4-methoxybenzenesulfonyl)(3-oxo-3-piperazin-1-ylpropyl)amino]-3-methylbutyramide hydrochloride, 375 mg (99%). $^1$H NMR (DMSO-d$_6$): δ 10.78 (br s, 1H), 9.16 (br s, 1H), 7.74 (d, J=8.8 Hz, 2H), 7.07 (d, J=8.9 Hz, 2H), 3.82 (s, 3H), 3.62 (br s, 4H), 3.38–3.18 (m, 1H), 3.16–3.07 (br s, 2H), 3.07–2.98 (br s, 2H), 2.83–2.73 (m, 1H), 2.65–2.53 (m, 1H), 2.06–1.90 (m, 1H), 0.76 (d, J=6.5 Hz, 3H), 0.72 (d, J=6.5 Hz, 3H). A broad water peak between δ 4.0 and 3.5 obscured some signals from this compound; MS (thermospray): m/z 443 M+H), 382, 328.

EXAMPLE 8

2-(R)-2-[(Benzylcarbamoylmethyl)(4-methoxybenzenesulfonyl)amino]-N-hydroxy-3-methylbutyramide To a solution of 2-(R)-2-[carboxymethyl(4-methoxybenzenesulfonyl)amino]-3-methylbutyric acid benzyl ester (example 1) (905 mg, 2.08 mmol) in methylene chloride (18 mL) were added sequentially triethylamine (0.72 mL, 5.14 mmol), benzylamine (0.25 mL, 2.29 mmol) and (benzotriazol-1-yloxy)tris(dimethylamino)phosphonium hexafluorophosphate (1.01 grams, 2.28 mmol). The mixture was stirred at room temperature overnight and then diluted with ethyl acetate. The solution was washed with 0.5 N hydrochloric acid solution and brine, dried over magnesium sulfate and concentrated under vacuum. The residue was chromatographed on silica gel using a 2:5:16 ratio of methylene chloride/ethyl acetate/hexane affording 2-(R)-2-[benzylcarbamoylmethyl)(4-methoxybenzenesulfonyl)amino]-3-methylbutyric acid benzyl ester as a clear oil, 933 mg (86%).

To a solution of 2-(R)-2-[(benzylcarbamoylmethyl)(4-methoxybenzenesulfonyl)amino]-3-methylbutyric acid benzyl ester (933 mg, 1.17 mmol) in ethanol (50 mL) was added 10% palladium on activated carbon (85 mg). The mixture was agitated under 3 atmospheres hydrogen in a Parr shaker for 4 hours. The catalyst was removed by filtration through nylon (pore size 0.45 μm) and the solvent was evaporated leaving 2-(R)-2-[(benzylcarbamoylmethyl)(4-methoxybenzenesulfonyl)amino]-3-methylbutyric acid as a white foam, 755 mg (98%).

To a solution of 2-(R)-2-[(benzylcarbamoylmethyl)(4-methoxybenzenesulfonyl)amino]-3-methylbutyric acid (655 mg, 1.51 mmol) and 1-hydroxybenztriazole hydrate (224 mg, 1.46 mmol) in dry dimethylformamide (15 mL) was added 1-(3-dimethylaminopropyl)-3-ethylcarbodiimide hydrochloride (316 mg, 1.65 mmol). After stirring for 30 minutes, hydroxylamine hydrochloride (416 mg, 6.0 mmol) and then N-methylmorpholine (0.99 mL, 9.0 mmol) were added. The mixture was stirred at room temperature overnight and then diluted with ethyl acetate. The solution was washed sequentially with water, 0.5 N hydrochloric acid solution and brine. The solution was then dried over magnesium sulfate and concentrated under vacuum to leave a white foam which was chromatographed on silica gel eluting with ethyl acetate to afford 2-(R)-2-[(benzylcarbamoylmethyl)(4-methoxybenzene-sulfonyl)amino]-N-hydroxy-3-methylbutyramide as a white foam, 570 mg (84%); $^1$H NMR (DMSO-d$_6$): δ10.75 (br s, 1H), 8.90 (s, 1H), 8.47 (m, 1H), 7.85 (d, J=8.9 Hz, 2H), 7.83–7.19 (m, 5H), 7.04 (d, J=8.9 Hz, 2H), 4.37 (d, J=11.4 Hz, 1H), 4.28 (d, J=5.9 Hz, 2H), 3.89 (d, J=11.4 Hz, 1H), 3.82 (s, 3H), 3.45 (d, J=10.3 Hz, 1H), 1.90–1.79 (m, 1H), 0.73 (d, J=6.3 Hz, 6H); MS (LSIMS): m/z 450 (M+H).

EXAMPLE 9

2-(R)-2-[(Benzylmethylcarbamoylmethyl)(4-methoxybenzenesulfonyl)amino]-N-hydroxy-3-methylbutyramide To a solution of 2-(R)-2-[carboxymethyl(4-methoxybenzenesulfonyl)amino]-3-methylbutyric acid benzyl ester (Example 1) (1.05 grams, 2.41 mmol) in methylene chloride (20 mL) were added sequentially triethylamine (0.84 mL, 6.0 mmol), N-benzylmethylamine (0.34 mL, 2.63 mmol) and (benzotriazol-1-yloxy)tris(dimethylamino)phosphonium hexafluorophosphate (1.17 grams, 2.69 mmol). The mixture was stirred at room temperature overnight and then diluted with ethyl acetate. The solution was washed with 0.5 N hydrochloric acid solution and brine, dried over magnesium sulfate and concentrated under vacuum. The residue was chromatographed on silica gel using 35% ethyl acetate in hexane (plus a small amount of methylene chloride to load the sample on the column) affording 2-(R)-2-[benzylmethylcarbamoylmethyl)(4-methoxybenzenesulfonyl)amino]-3-methylbutyriacid benzyl ester as a clear oil, 1.14 grams (88%).

To a solution of 2-(R)-2-[(benzylmethylcarbamoylmethyl)(4-methoxybenzenesulfonyl)amino]-3-methylbutyric acid benzyl ester (1.14 grams, 2.12 mmol) in ethanol (100 mL) was added 10% palladium on activated carbon (400 mg). The mixture was agitated under 3 atmospheres hydrogen in a Parr shaker for 3 hours. The catalyst was removed by filtration through nylon (pore size 0.45 μm) and the solvent was evaporated leaving 2-(R)-2-[(benzylmethylcarbamoylmethyl)(4-methoxybenzenesulfonyl)amino]-3-methylbutyric acid as a white foam, 902 mg (95%).

To a solution of 2-(R)-2-[(benzylmethylcarbamoylmethyl)(4-methoxybenzenesulfonyl)amino]-3-methylbutyric acid (902 mg, 2.01 mmol) in methylene chloride (20 mL) were added sequentially triethylamine (0.90 mL, 6.42 mmol), O-allylhydroxylamine hydrochloride (242 mg, 2.21 mmol) and (benzotriazol-1-yloxy)tris(dimethylamino)phosphonium hexafluorophosphate (978 mg, 2.21 mmol). The mixture was stirred at room temperature overnight and then diluted with ethyl acetate. The solution was washed with 0.5 N hydrochloric acid solution and brine, dried over magnesium sulfate and concentrated under vacuum. The residue was chromatographed on silica gel using 40% hexane in ethyl acetate to afford 2-(R)-N-allyloxy-2-[(benzylmethylcarbamoylmethyl)(4-methoxy-benzenesulfonyl)amino]-3-methylbutyramide as an oil, 1.008 grams (100%).

To a solution of 2-(R)-N-allyloxy-2-[(benzylmethylcarbamoylmethyl)(4-methoxybenzenesulfonyl)amino]-3-methylbutyramide (500 mg, 0.99 mmol) in methylene chloride (40 mL) was added bis(triphenylphosphine)palladium (II) chloride (280 mg, 0.4 mmol) and then, dropwise, tributyltinhydride (0.43 mL, 2.2 mmol). The solution was stirred at room temperature for 1 hour, diluted with methylene chloride, washed with 1N hydrochloric acid solution, dried over magnesium sulfate and concentrated. The residue was taken up in ethyl acetate and filtered to remove a solid. After concentration, the filtrate was chromatographed on silica gel eluting with chloroform and then 2% methanol in chloroform to afford 2-(R)-2-[(benzylmethylcarbamoylmethyl)(4-methoxybenzenesulfonyl)amino]-N-hydroxy-3-methylbutyramide as a white solid (340 mg, 74%). $^1$H NMR (DMSO-$d_6$): δ 10.66 (br s, 1H), 8.87 (br s, 0.6H), 8.84 (s, 0.4H), 7.91 (d, J=8.9 Hz, 1.2H), 7.78 (d, J=8.9 Hz, 0.8H), 7.43–7.21 (m, 5H), 7.05 (d, J=8.9 Hz, 1.2H), 7.00 (d, J=8.9 Hz, 0.8H) 4.72 (d, J=17.7 Hz, 0.4H), 4.70 (d, J=17.7 Hz, 0.6H), 4.59–4.42 (m, 1H), 4.25 (d, J=17.8 Hz, 0.6H), 4.07 (d, J=17.7 Hz, 0.4H), 3.82 (s, 3H), 3.46–3.40 (m, 1H), 2.91 (s, 1.8H), 2.83 (s, 1.2H), 1.92–1.70 (m, 1H), 0.75–0.69 (m, 6H); MS (thermospray): m/z 464 (M+H), 307, 239.

The title compounds of Examples 10–11 were prepared by a method analogous to that described in Example 9 using 2(R)-2-[carboxymethyl(4-methoxybenzenesulfonyl) amino]-3-methylbutyric acid benzyl ester (example 1) as the starting material which is coupled with the amine indicated.

EXAMPLE 10

2-(R)-N-Hydroxy-2-([4-methoxybenzenesulfonyl]-[(2-morpholin-4-ylethylcarbamoyl)methyl]amino)-3-methylbutyramide Coupled with 4-(2-aminoethyl)morpholine: $^1$H NMR (DMSO-$d_6$): δ 10.74 (br s, 1H), 8.90 (br s, 1H), 7.84 (br s, 1H, overlapped ), 7.84 (d, J=8.8 Hz, 2H), 7.06 (d, J=8.8 Hz, 2H), 4.33 (d, J=17.5 Hz, 1H), 3.83 (s, 3H), 3.78 (d, J=17.5 Hz, 1H), 3.57–3.54 (m, 4H), 3.49 (d, J=10.2 Hz, 1H), 2.38–3.06 (m, 2H), 3.24–2.30 (m, 6H), 1.93–1.77 (m, 1H), 0.77–0.74 (m, 6H).

EXAMPLE 11

2-(R)-N-Hydroxy-2-[(4-methoxybenzenesulfonyl)(2-oxo-2-pyrrolidin-1-ylethyl)amino]-3-methylbutyramide Coupled with pyrrolidine: $^1$H NMR (CD$_3$OD): δ 7.90 (d, J=8.9 Hz, 2H), 7.04 (d, J=8.9 Hz, 2H), 4.50 (d, J=17.6 Hz, 1H), 4.15 (d, J=17.6 Hz, 1H), 3.87 (s, 3H), 3.56–3.39 (m, 5H), 2.07–1.82 (m, 5H), 0.83 (d, J=6.6 Hz, 3H), 0.73 (d, J=6.6 Hz, 3H); MS (thermospray): m/z 414 (M+1); HRMS calculated for $C_{18}H_{28}N_3O_6S$ (M+H): 414.1699. Found 414.1703.

EXAMPLE 12

2-[Dimethylcarbamoylmethyl(4-methoxybenzenesulfonyl) amino]-N-hydroxy-3-methyl-butyramide A solution of 2-(R)-2-[carboxymethyl(4-methoxybenzenesulfonyl)amino]-3-methylbutyric acid benzyl ester (Example 1) (1.89 grams, 4.34 mmol) in thionyl chloride (25 mL) was heated at reflux for 1 hour. After cooling, the excess thionyl chloride was evaporated. The residue was taken up in methylene chloride (50 mL) and the solution was cooled in an ice bath. Dimethylamine gas was slowly bubbled through the solution for 1 hour. After evaporation of the solvent, the residue was taken up in ethyl acetate, washed with 1 N hydrochloric acid solution, water and brine, dried over magnesium sulfate and concentrated to leave dimethylcarbamoylmethyl(4-methoxybenzenesulfonyl)amino-3-methylbutyric acid benzyl ester as an oil, 1.77 grams (88%).

To a solution of dimethylcarbamoylmethyl(4-methoxybenzenesulfonyl)amino-3-methylbutyric acid benzyl ester (1.77 grams, 3.83 mmol) in ethanol (100 mL) was added 10% palladium on activated carbon (644 mg). The mixture was agitated under 3 atmospheres hydrogen in a Parr shaker for 1.5 hours. The catalyst was removed by filtration through nylon (pore size 0.45 μm) and the solvent was evaporated leaving dimethylcarbamoylmethyl(4-methoxybenzenesulfonyl)amino-3-methylbutyric acid as a white foam, 1.42 grams (100%).

To a solution of dimethylcarbamoylmethyl(4-methoxybenzenesulfonyl)amino-3-methylbutyric acid (1.42 grams, 3.81 mmol) and 1-hydroxybenztriazole hydrate (687 mg, 4.48 mmol) in dry dimethylformamide (7 mL) was added 1-(3-dimethylaminopropyl)-3-ethyolcarbodiimide hydrochloride (974 mg, 5.08 mmol). After stirring for 30 minutes, hydroxylamine hydrochloride (1.17 grams, 16.8 mmol) and then N-methylmorpholine (2.8 mL, 25.5 mmol) were added. The mixture was stirred at room temperature overnight and then concentrated under vacuum. The residue was taken up in ethyl acetate and the resulting solution was washed sequentially with water, 0.5 N hydrochloric acid solution and brine. The solution was then dried over magnesium sulfate and concentrated under vacuum to leae an oil which was chromatographed on silica gel eluting successively with ethyl acetate, 5% methanol in chloroform and 10% methanol in chloroform to afford 2-[dimethylcarbamoylmethyl(4-methoxybenzenesulfonyl)amino]-N-hydroxy-3-methylbutyramide as a white solid, 390 mg (26%). $^1$H NMR (DMSO-$d_6$): δ 10.70 (br s, 1H), 8.89 (s, 1H), 7.80 (d, J=8.9 Hz, 2H), 7.10 (d, J=8.9 Hz, 2H), 4.62 (d, J=17.7 Hz, 1H), 4.14 (d, J=17.7 Hz, 1H), 3.84 (s, 3H), 3.40 (d, J=10.4 Hz, 1H), 2.97 (s, 3H), 2.82 (s, 3H), 1.88–1.72 (m, 1H), 0.72 (d, J=6.5 Hz, 6H); MS (thermospray): m/z 388 (M+1); HRMS calculated for $C_{16}H_{26}N_3O_6S$ (M+H): 388.1542. Found: 388.1592.

EXAMPLE 13

2-(R)-N-Hydroxy-2-((4-methoxybenzenesulfonyl) ([(pyridin-3-ylmethyl)carbamoyl]methyl)amino)-3-methylbutyramide 2-(R)-N-Hydroxy-2-((4-methoxybenzenesulfonyl) ([(pyridin-3-ylmethyl)carbamoyl]methyl)amino)-3-methylbutyramide was prepared by a procedure similar to that of Example 12 starting with 2-(R)-2-[carboxymethyl(4-methyoxybenzenesulfonyl)amino]-3-methylbutyric acid benzyl ester (Example 1) and coupling this to 3-pyridylmethylamine via the acid chloride. $^1$H NMR (CD$_3$OD): δ 8.55–8.53 (m, 1H), 8.43–8.40 (m, 1H), 7.90–7.82 (m, 1H, overlapped), 7.86 (d, J=8.9 Hz, 2H), 7.40 (dd, J=4.8, 7,8 Hz, 1H), 7.04 (d, J=8.9 Hz, 2H), 4.50 (d, J=17.5 Hz, 1H), 4.39 (d, J=17.5 Hz, 1H), 4.32 (d, J=17.7 Hz, 1H), 4.02 (d, J=17.7 Hz, 1H), 3.87 (s, 3H), 3.60 (d, J=10.3 Hz, 1H), 2.08–1.93 (m, 1H), 0.85 (d, J=6.5 Hz, 3H), 0.70 (d, J=6.5 Hz, 3H); MS (thermospray): m/z 451 (M+H), 336, 320.

EXAMPLE 14

N-Hydroxy-[(4-methoxybenzenesulfonyl)(2-morpholin-4-yl-2-oxoethyl)amino]acetamide To a solution of iminoacetic acid disodium salt monohydrate (5.0 grams, 25.6 mmol) in dioxane (50 ml) and water (50 ml) was added triethylamine (5.3 ml, 38 mmol) followed by 4-methoxybenzenesulfonyl chloride (5.8 grams, 28.0 mmol). The mixture was stirred overnight at room temperature and diluted with methylene chloride. The solution was washed with 1 N hydrochloric acid solution, water and brine, dried over magnesium sulfate and concentrated under vacuum leaving [carboxymethyl(4-methoxybenzenesulfonyl) amino]acetic acid as a white solid, 3.83 grams (49%).

[Carboxymethyl(4-methoxybenzenesulfonyl)amino] acetic acid (0.5 grams, 1.65 mmol) in acetic anhydride (15 mL) was dissolved in acetic anhydride by gentle warming. The resulting solution was stirred at room temperature overnight. The acetic anhydride was removed by evaporation under vacuum; the residue was dissolved in methylene chloride and morpholine (0.16 mL, 1.82 mmol) was added. The mixture was stirred overnight at room temperature and then concentrated under vacuum. The residue was dissolved in ethyl acetate, washed with 1N hydrochloric acid solution, water and brine, dried over magnesium sulfate and concentrated to afford [(4-methoxybenzenesulfonyl)(2-morpholin-4-yl-2-oxoethyl)amino]acetic acid as an oil, 0.33 grams (54%).

To a solution of [(4-methoxybenzenesulfonyl)(2-morpholin-4-yl-2-oxoethyl)amino]acetic acid (0.33 grams, 0.89 mmol) in methylene chloride (10 mL) were added sequentially triethylamine (0.43 mL, 3.1 mmol), O-benzylhydroxylamine hydrochloride (0.15 grams, 0.94 mmol) and (benzotriazol-1-yloxy)tris(dimethylamino) phosphonium hexafluorophosphate (0.43 grams, 0.97 mmol). The mixture was stirred at room temperature overnight and then diluted with ethyl acetate. The solution was washed sequentially with 0.5 N hydrochloric acid solution, water and brine, dried over magnesium sulfate and concentrated under vacuum. The residue was chromatographed on silica gel using ethyl acetate to afford N-benzyloxy-[(4-methoxybenzenesulfonyl)(2-morpholin-4-yl-2-oxoethyl) amino]acetamide as a white solid, 0.33 grams (78%).

To a solution of N-benzyloxy-[(4-methoxybenzenesulfonyl)(2-morpholin-4-yl-2-oxoethyl) amino]acetamide (0.33 grams, 0.69 mmol) in methanol (35 mL) was added 5% palladium on activated carbon (85 mg). The mixture was agitated under 2 atmospheres hydrogen in a Parr shaker for 1.5 hours. The catalyst was removed by filtration through nylon (pore size 0.45 μm) and the solvent was evaporated. The residue was chromatographed on silica gel eluting with 5% methanol in methylene chloride to afford N-methoxy-[(4-methoxybenzenesulfonyl)(2-morpholin-4-yl-2-oxoethyl)amino]acetamide as a white solid, 65 mg (24%); $^1$H NMR (CD$_3$OD): δ7.82 (d, J=9.0 Hz, 2H), 7.08 (d, J=9.0 Hz, 2H), 4.24 (s, 2H), 3.88 (s, 3H), 3.84 (s, 2H), 3.68–3.64 (m, 4H), 3.58–3.50 (m, 4H); MS (thermospray): m/z 388 (M+1), 387 (M); HRMS calculated for C$_{16}$H$_{22}$N$_3$O$_7$S (M+H): 388.1178, Found 338.1180.

The title compounds of Examples 15–16 were prepared by a method analogous to that described in Example 14 using [carboxymethyl(4-methoxybenzenesulfonyl)amino] acetic acid as the starting material which, after treatment with acetic anhydride, is coupled with the amine indicated.

EXAMPLE 15

N-Hydroxy-[(4-methoxybenzenesulfonyl)(2-oxo-2-pyrrolidin-1-ylethyl)amino]acetamide Coupled with pyrrolidine: $^1$H NMR (DMSO-d$_6$): δ 11.26 (br s, 1H), 8.89 (s, 1H), 7.81 (d, J=8.9 Hz, 2H), 7.10 (d, J=8.9 Hz, 2H), 4.09 (s, 2H), 3.85 (s, 3H), 3.74 (s, 2H), 3.45–3.25 (m, 4H), 1.93–1.72 (m, 4H); MS (thermospray): m/z 372 (M+1): Analysis calculated for C$_{15}$H$_{21}$N$_3$O$_6$S: C, 48.51; H, 5.70; N, 11.31. Found: C, 48.51; H, 5.82; N, 11.24.

EXAMPLE 16

2-[Dimethylcarbamoylmethyl(4-methoxybenzenesulfonyl) amino]-N-hydroxyaccetamide

Coupled with dimethylamine: mp: 170° C. (dec.); $^1$H NMR (DMSO-d$_6$): δ 10.69 (br s, 1H), 8.88 (s, 1H), 7.91 (d, J=8.9 Hz, 2H), 7.06 (d, J=8.9 Hz, 2H), 4.19 (s, 2H), 3.85 (s, 3H), 3.73 (s, 2H), 2.94 (s, 3H), 2.84 (s, 3H); MS (thermospray): m/z 346 (M+1); Analysis calculated for C$_{13}$H$_{19}$N$_3$O$_6$S: C, 45.21; H, 5.55 N, 12.17. Found: C, 44.93, H, 5.61; N, 12.03.

EXAMPLE 17

2-(R)-2-[(2-Carbamoylethyl)(4-methoxybenzenesulfonyl) amino]-N-hydroxy-3-methylbutyramide To a solution of 2-(R)-2-[(2-carboxyethyl(4-methoxybenzenesulfonyl)amino]-3-methylbutyric acid benzyl ester (example 2) (900 mg., 2.0 mmol) in methylene chloride (10 mL) was added thionyl chloride (0.16 mL, 2.2 mmol). The reaction mixture was stirred for 1.5 hours at room temperature and then concentrated in vacuo. After dissolving the residue in methylene chloride (10 mL), ammonia gas was bubbled through the solution for 0.5 minutes. The solution was stirred at room temperature overnight and was concentrated under vacuum. Flash chromatography of the residue on silica gel eluting with 2% methanol in chloroform provided 2-(R)-2-[(2-carbamoylethyl) (4-methoxybenzenesulfonyl)amino]-N-hydroxy-3-methylbutyric acid benzyl ester as a clear oil (275 mg, 31%).

To a solution of 2-(R)-2-[(2-carbamoylethyl)(4-methoxybenzenesulfonyl)amino]-N-hydroxy-3-methylbutyric acid benzyl ester (275 mg, 0.61 mmol) in ethanol (15 mL) was added 10% palladium on activated carbon (30 mg). The mixture was agitated under 3 atmospheres hydrogen in a Parr shaker for 5 hours. The catalyst was removed by filtration through diatomaceous earth and the solvent was evaporated leaving 2-(R)-2-[(2-carbamoylethyl) (4-methoxybenzenesulfonyl)amino]-N-hydroxy-3-methylbutyric acid as a white foam, 211 mg (96%).

To a solution of 2-(R)-2-[2-carbamoylethyl)(4-methoxybenzenesulfonyl)amino]-N-hydroxy-3-methylbutyric acid (205 mg, 0.57 mmol) and 1-hydroxybenztriazole hydrate (85 mg, 0.55 mmol) in dry dimethylformamdie (5 mL) was added 1-(3-dimethylaminopropyl)-3-ethylcarbodiimide hydrochloride (120 mg, 0.63 mmol). After stirring for 30 minutes, hydroxylamine hydrochloride (158 mg, 2.3 mmol) and then N-methylmorpholine (0.37 mL, 3.4 mmol) were added. The mixture was stirred at room temperature overnight and then diluted with ethyl acetate. The solution was washed with water and brine. The solution was then dried over magnesium sulfate and concentrated under vacuum to leave an oil which was chromatographed on silica gel eluting with 2% methanol in chloroform to afford 2-(R)-2-[(2-carbamoylethyl)(4-methoxybenzenesulfonyl)amino]-N-hydroxy-3-methylbutyramide as a while solid, 45 mg (21%); $^1$H NMR (DMSO-d$_6$): δ 10.74 (br s, 1H), 8.91 (br s, 1H), 7.74 (d, J=8.8 Hz, 2H), 7.33 (br s, 1H), 7.07 (d, J=8.8 Hz, 2H), 6.79 (br s, 1H), 3.93–3.82 (m, 1H, overlapped), 3.83 (s, 3H), 3.64 (d, J=10.7 Hz, 1H), 3.25–3.12 (m, 1H), 2.62–2.48 (m, 1H), 2.42–2.30 (m, 1H), 2.06–1.94 (m, 1H), 0.79 (d, J=6.6 Hz, 3H), 0.76 (d, J=6.6 Hz, 3H); MS (thermospray): m/z 374 (M+H).

EXAMPLE 18

2-(R)-2-[(2-tert-Butoxycarbonylethyl)(4-methoxybenzenesulfonyl)-amino]-N-hydroxy-3-methylbutyramide A solution of N,N-dimethylformamide di-tert-butyl acetal (1.9 mL, 7.9 mmol) in toluene (1.5 mL) was added dropwise to a solution of 2-(R)-2-[(2-carboxyethyl(4-methoxybenzenesulfonyl)amino]-3-methylbutyric acid benzyl ester (example 2) 900 mg, 2.0 mmol) in toluene at 80° C. After heating for 2 hours at 80° C., the mixture was cooled and concentrated to leave an amber oil which was chromatographed on silica gel eluting with chloroform to afford (2-(R)-2-[(2-tert-butoxycarbonylethyl)(4-methoxybenzenesulfonyl) amino]-3-methylbutyric acid benzyl ester as an oil, 3.75 mg (37%).

To a solution of 2-(R)-2-[(2-tert-butoxycarbonylethyl)(4-methoxybenzenesulfonyl)-amino]-3-methylbutyric acid benzyl ester (370 mg, 0.73 mmol) in ethanol (20 mL) was added 10% palladium on activated carbon (40 mg). The mixture was agitated under 3 atmospheres hydrogen in a Parr shaker for 5 hours. The catalyst was removed by filtration through diatomaceous earth and the solvent was evaporated leaving 2-(R)-2-[(2-tert-butoxycarbonylethyl)(4-methoxybenzenesulfonyl)amino]-3-methylbutyric acid as a white foam, 30 mg (100%).

To a solution of 2-(R)-2-[(2-tert-butoxycarbonylethyl)(4-methoxybenzenesulfonyl)amino]-3-methylbutyric acid (303 mg, 0.73 mmol) and 1-hydroxybenztriazole hydrate (108 mg, 0.70 mmol) in dry dimethylformamide (10 mL) was added 1-(3-dimethylaminopropyl)-3-ethylcarbodiimide hydrochloride (153 mg, 0.80 mmol). After stirring for 45 minutes, hydroxylamine hydrochloride (203 mg, 2.9 mmol) and then N-methylmorpholine (0.48 mL, 4.4 mmol) were added. The mixture was stirred at room temperature overnight and then concentrated under vacuum. The residue was chromatographed on silica gel eluting with 2% methanol in chloroform and again with 10% ethyl acetate in hexane to afford 2-(R)-2-[(2-tert-butoxycarbonylethyl)(4-methoxybenzenesulfonyl)amino]-N-hydroxy-3-methylbutyramide as a white foam, 135 mg (43%); $^1$H NMR (DMSO-d$_6$): δ10.77 (br s 1H), 7.74 (d, J=8.9 Hz, 2H), 7.08 (d, J=8.9 Hz, 2H), 3.93–3.82 (m, 1H, overlapped), 3.83 (s, 3H), 3.64 (d, J=10.8 Hz, 1H), 3.26–3.14 (m, 1H), 2.70–2.60 (m, 1H), 2.50–2.38 (m, 1H), 2.04–1.91 (m, 1H), 1.38 (s, 9H), 0.78 (d, J=6.5 Hz, 3H), 0.72 (d, J=6.5 Hz, 3H); MS (thermospray): m/z 431 (M+H), 375, 314.

EXAMPLE 19

2-(R)-2-[2-Carboxyethyl(4-methoxybenzenesulfonyl) amino]-N-hydroxy-3-methylbutyramide To a solution of 2-(R)-2-[2-tert-butoxycarbonylethyl)(4-methoxybenzenesulfonyl)amino]-N-hydroxy-3-methylbutyramide (example 18) (100 mg), 0.23 mmol) in methylene chloride (1 mL) at 0° C. was added to trifluoracetic acid (1 mL). The mixture was allowed to warm to room temperature while stirring overnight. After evaporation of the triifluroracetic acid and methylene chloride, the residue was chromatographed on silica gel eluting with 5% methanol in chloroform. Concentration of the appropriate fractions afforded 2-(R)-2-[2-carboxyethyl(4-methoxybenzenesulfonyl)-amino]-N-hydroxy-3-methylbutyramide as a white solid, 35 mg (41%). $^1$H NMR (DMSO-D$_6$): δ 10.79 (br s, 1H), 8.97 (br s, 1H), 7.76 (d, J=8.9 Hz, 2H), 7.09 (d, J=8.9 Hz, 2H), 3.95–3.82 (m, 1H, overlapped), 3.84 (s, 3H), 3.66 (d, J=10.8 Hz, 1H), 3.30–3.20 (m, 1H), 2.73–2.63 (m, 1H), 2.50–2.40 (m, 1H), 2.07–1.94 (m, 1H), 0.80 (d, J=6.5 Hz, 3H), 0.74 (d, J=6.5 Hz, 3H); MS (thermospray): m/z 375 (M+H), 314.

What is claimed is:

1. A compound of the formula

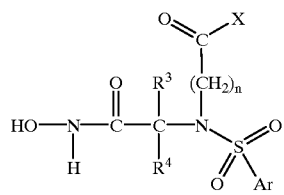

I or the pharmaceutically acceptable salts thereof wherein n is 1 to 6

X is hydroxy, $(C_1-C_6)$alkoxy or $NR^1R^2$ wherein $R^1$ and $R^2$ are each independently selected from the group consisting of hydrogen, $(C_1-C_6)$alkyl, piperidyl, $(C_1-C_6)$alkylpiperidyl, $(C_6-C_{10})$arylpiperidyl, $(C_5-C_9)$heteroarylpiperidyl, $(C_6-C_{10})$aryl$(C_1-C_6)$alkylpiperidyl,$(C_5-C_9)$heteroaryl$(C_1-C_6)$alkylpiperidyl, $(C_1-C_6)$acylpiperidyl,$(C_6-C_{10})$aryl, $(C_5-C_9)$heteroaryl,$(C_6-C_{10})$aryl$(C_1-C_6)$alkyl,$(C_5-C_9)$heteroaryl$(C_1-C_6)$alkyl,$(C_6-C_{10})$aryl$(C_6-C_{10})$aryl, $(C_6-C_{10})$aryl$(C_6-C_{10})$aryl$(C_1-C_6)$alkyl, $(C_3-C_6)$cycloalkyl, $(C_3-C_6)$cycloalkyl$(C_1-C_6)$alkyl, $R^5(C_2-C_6)$alkyl,$(C_1-C_5)$alkyl$(CHR^5)(C_1-C_6)$alkyl wherein $R^5$ is hydroxy, $(C_1-C_6)$acyloxy, $(C_1-C_6)$(alkoxy, piperazino, $(C_1-C_6)$acylamino, $(C_1-C_6)$alkythio, $(C_6-C_{10})$arylthio, $(C_1-C_6)$alkylsulfinyl, $(C_6-C_{10})$arysulfinyl, $(C_1-C_6)$alkylsulfoxyl $(C_6-C_{10})$arylsulfoxyl amino, $(C_1-C_6)$alkylamino, $((C_1-C_6)$alkyl$)_2$ amino, $(C_1-C_6)$acylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$ alkylpiperazino, morpholino, thiomorpholino, piperidino or pyrrolidino; $R^6(C_1-C_6)$alkyl, $(C_1-C_5)$alkyl$(CHR^6)(C_1-C_6)$alkyl wherein $R^6$ is piperidyl, $(C_1-C_6)$alkylpiperidyl, $(C_6-C_{10})$arylpiperidyl, $(C_6-C_{10})$aryl$(C_1-C_5)$alkylpiperidyl, $(C_5-C_9)$heteroarylpiperidyl or $(C_5-C_9)$heteroaryl$(C_1-C_6)$alkylpiperidyl; and $CH(R^7)COR^8$ wherein $R^7$ is hydrogen, $(C_1-C_6)$alykl, $(C_6-C_{10})$aryl $(C_1-C_6)$alkyl, $(C_5-C_9)$heteroaryl$(C_1-C_6)$alkyl, $(C_1-C_6)$alkythio$(C_1-C_6)$alkyl, $(C_5-C_{10})$arylthio $(C_1-C_6)$alkyl, $(C_1-C_6)$alkylsulfinyl$(C_1-C_6)$alkyl, $(C_6-C_{10})$ arylsulfinyl$(C_1-C_6)$alkyl, $(C_1-C_6)$alkylsulfonyl$(C_1-C_6)$alkyl, $(C_6-C_{10})$arylsulfonyl $(C_1-C_6)$alkyl, hydroxy$(C_1-C_6)$alkyl, amino$(C_1-C_6)$alkyl, $(C_1-C_6)$alkylamino$(C_1-C_6)$alkyl, $((C_1-C_6)$alkylamino$)_2(C_1-C_6)$alkyl,$R^9R^{10}NCO(C_1-C_6)$alkyl or $R^9OCO(C_1-C_6)$alkyl wherein $R^9$ and $R^{10}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl; and $R^8$ is $R^{11}O$ or $R^{11}R^{12}N$ wherein $R^{11}$ and $R^{12}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl;

or $R^1$ and $R^2$, or $R^9$ and $R^{10}$, or $R^{11}$ and $R^{12}$ may be taken together to form an azetidinyl, pyrrolidinyl, morpholinyl, thiomorpholinyl, indolinyl, isoindolinyl, tetrahydroquinolinyl, tetrahydroisoquinolinyl, $(C_1-C_6)$ acylpiperazinyl, $(C_1-C_6)$alkylpiperazinyl, $(C_6-C_{10})$ arylpiperazinyl, $(C_5-C_9)$heteroarylpiperazinyl or a bridged diazabicycloalky ring selected from the group consisting of

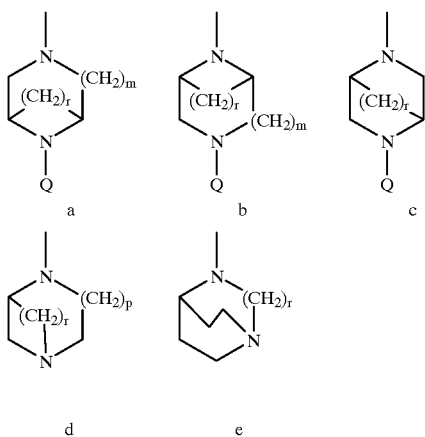

wherein r is 1, 2 or 3;
m is 1 or 2;
p is 0 or 1; and
Q is hydrogen, $(C_1-C_3)$alkyl or $(C_1-C_6)$acyl;
$R^3$ and $R^4$ are taken together to form an indanyl or tetralinyl ring or a group of the formula

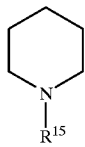

wherein $R^{15}$ is hydrogen, $(C_1-C_6)$acyl, $(C_1-C_6)$alkyl, $(C_6-C_{10})$aryl$(C_1-C_6)$alkyl, $(C_5-C_9)$heteroaryl$(C_1-C_6)$alkyl or $(C_1-C_6)$alkylsulfonyl; and Ar is $(C_6-C_{10})$aryl, $(C_5-C_9)$heteroaryl, $(C_1-C_6)$alkyl$(C_6-C_{10})$aryl, $(C_1-C_6)$alkoxy$(C_6-C_9)$aryl, $((C_1-C_6)$alkoxyl$)(C_6-C_{10})$aryl, $(C_6-C_{10})$aryloxy$(C_6-C_{10})$aryl, $(C_5-C_9)$heteroaryloxy$(C_6-C_{10})$aryl, $(C_1-C_6)$alkyl$(C_5-C_9)$heteroaryl, $(C_1-C_6)$alkoxy$(C_5-C_9)$heteroaryl, $((C_1-C_6)$alkoxy$)_2(C_5-C_9)$heteroaryl, $(C_6-C_{10})$aryloxy$(C_5-C_9)$heteroaryl, $(C_5-C_9)$heteroaryloxy$(C_5-C_9)$heteroaryl;

with the priviso that when either $R^1$ or $R^2$ is CH($R^7$)COR$^6$ wherein $R^7$ and $R^8$ are as defined above, the other of $R^1$ or $R^2$ is hydrogen, $(C_1-C_6)$alkyl or benzyl.

2. A compound according to claim 1, wherein n is 2.

3. A compound according to claim 1, wherein Ar is 4-methoxyphenyl or 4-phenoxyphenyl.

4. A compound according to claim 1, wherein n is 1 and either $R^1$ or $R^2$ is hydrogen.

5. A pharmaceutical composition for (a) the treatment of a condition selected from the group consisting of arthritis, cancer, tissue ulceration, restenosis, peridontal disease, epidermolysis bullosa, scleritis and other diseases characterized by matrix metalloproteinase activity, sepsis, septic shock and other diseases involving the production of tumor necrosis factor (TNF) or (b) the inhibition of matrix metalloproteinases or the production of tumor necrosis factor (TNF) in a mammal, comprising an amount of a compound of claim 1 or a pharmaceutically acceptable salt thereof, effective in such treatments and a pharmaceutically acceptable carrier.

6. A method for the inhibition of (a) matrix metalloproteinases or (b) the production of tumor necrosis factor (TNF) in a mammal comprising administering to said mammal an effective amount of a compound of claim 1 or a pharmaceutically acceptable salt thereof.

7. A method for treating a condition selected from the group consisting of arthritis, cancer, tissue ulceration, restenosis, peridontal disease, epidermolysis bullosa, scleritis and other diseases characterized by matrix metalloproteinase activity, sepsis, septic shock and other diseases involving the production of tumor necrosis factor (TNF) in a mammal comprising administering to said mammal an amount of a compound of claim 1 or a pharmaceutically acceptable salt thereof, effective in treating such a condition.

* * * * *